United States Patent [19]

Loomans et al.

[11] Patent Number: 4,708,966
[45] Date of Patent: Nov. 24, 1987

[54] NOVEL ANTI-INFLAMMATORY AGENTS, PHARMACEUTICAL COMPOSITIONS AND METHODS FOR REDUCING INFLAMMATION

[75] Inventors: Maurice E. Loomans; Randall S. Matthews, both of Cincinnati; Joseph A. Miller, Fairfield, all of Ohio

[73] Assignee: The Procter & Gamble Company, Cincinnati, Ohio

[21] Appl. No.: 879,863

[22] Filed: Jun. 27, 1986

[51] Int. Cl.$^4$ .............................................. A61K 31/12
[52] U.S. Cl. ..................... 514/689; 560/142; 560/130; 558/415; 558/416; 558/427; 558/436; 558/441; 568/775; 568/784; 568/308; 568/337; 568/662; 568/663; 568/627; 564/342; 564/366; 564/372; 564/374; 564/285; 564/223; 564/169; 260/410.5; 562/463; 514/545; 514/546; 514/733; 514/678; 514/649; 514/643; 514/629; 514/621; 514/570
[58] Field of Search ............... 560/142, 130; 558/415, 558/416, 427, 430, 441; 568/775, 784, 308, 337, 662, 663, 627; 564/342, 366, 372, 374, 285, 223, 169; 260/410.5; 562/403; 514/545, 546, 733, 678, 689, 649, 643, 629, 621, 570

[56] References Cited

U.S. PATENT DOCUMENTS

| | | | |
|---|---|---|---|
| Re. 27,004 | 12/1970 | Meier et al. | 568/308 |
| 3,226,443 | 2/1965 | Meier et al. | 568/308 |
| 3,335,164 | 8/1967 | Scherer et al. | 560/130 |
| 3,477,991 | 11/1969 | Patton et al. | 568/780 |
| 3,526,668 | 9/1970 | Starnes et al. | 568/784 |
| 3,660,505 | 5/1972 | Starnes et al. | 568/784 |
| 3,714,122 | 1/1973 | Kline | 568/308 |
| 4,130,666 | 12/1978 | Moore | 424/331 |
| 4,172,151 | 10/1979 | Moore | 514/689 |
| 4,440,784 | 4/1984 | Katsumi et al. | 424/300 |

FOREIGN PATENT DOCUMENTS

| | | | |
|---|---|---|---|
| 53-141234 | 12/1978 | Japan | 558/390 |
| 60-54315 | 3/1985 | Japan | 424/300 |

OTHER PUBLICATIONS

Hauff et al., Chem. Ber., 105 (4), pp. 1446–1455 (1972); and CAS Abstract No. 76: 153273k.
Gavrilov et al., Khim.-Farm. Zh., 12 (9), pp. 42–45 (1978).
Swingle et al., in "Anti-Inflammatory and Anti-Rheumatic Drugs, vol. III" (K. D. Rainsford, Editor; CRC Press, Inc.; 1985), pp. 105–126.

Primary Examiner—James H. Reamer
Attorney, Agent, or Firm—Kim W. Zerby; George W. Allen; Jack D. Schaeffer

[57] ABSTRACT

The present invention relates to novel specifically-substituted phenyl compounds, especially substituted di-tert-butyl phenol derivatives, which are effective as anti-inflammatory, analgesic and/or antipyretic agents. These phenyl compounds are substituted with a low molecular weight alkyl chain which terminates in a specific unsaturated functional group. These unsaturated functionalities are —C≡CH, C=CH$_2$, C=C=CH$_2$, and aldehydes in the form of their acetals.

The present invention further relates to pharmaceutical compositions which contain an anti-inflammatory agent of the present invention and a pharmaceutically-acceptable carrier.

Finally, the present invention relates to methods for treating diseases characterized by inflammation, such as rheumatoid arthritis and osteoarthritis, in humans or lower animals. Such methods comprise administering to a human or lower animal in need of such treatment a safe and effective amount of an anti-inflammatory agent or composition of the present invention.

24 Claims, No Drawings

NOVEL ANTI-INFLAMMATORY AGENTS, PHARMACEUTICAL COMPOSITIONS AND METHODS FOR REDUCING INFLAMMATION

BACKGROUND OF THE INVENTION

The present invention relates to novel specifically-substituted phenyl compounds, especially substituted di-tert-butyl phenol derivatives, which are effective as anti-inflammatory, analgesic and/or antipyretic agents. The present invention further relates to pharmaceutical compositions which are useful for treating diseases which involve inflammation, pain, and/or fever. Finally, the present invention relates to methods for treating diseases characterized by inflammation.

The search for new non-steroidal anti-inflammatory ("NSAI") drugs over the last 10 to 20 years has led to the testing by various researchers and companies of thousands of compounds for efficacy as anti-inflammatories. The search has raised many questions, but provided few answers, about how and why some compounds are efficacious and others are not, especially for substituted di-tert-butyl phenol derivatives. This search, and the results and questions raised thereby, are discussed more fully in "Anti-inflammatory Activity of Anti-oxidants", by K. F. Swingle, et al., Chapter 4 of *Anti-inflammatory and Anti-rheumatic Drugs*, Vol. III (K. D. Rainsford, Editor; CRC Press, Inc.; 1985), pages 105–126, which is incorporated herein by reference.

Notwithstanding the great effort already put forth to identify NSAI drugs, there remains a continuing need to identify new compounds and compositions which are effective for treating inflammation and inflammatory diseases such as rheumatoid arthritis and osteorthritis. It is accordingly an object of the present invention to provide compounds which are effective anti-inflammatory agents, as well as pharmaceutical compositions containing these compounds. It is a further object of the present invention to provide methods for treating diseases characterized by inflammation.

It is further object of the present invention to provide compounds which are useful as anti-inflammatory agents, analgesic agents, antipyretic agents, antioxidant agents, antiarthritic agents, bone modifying agents, and/or immunomodulating agents, and pharmaceutical compositions containing these compounds. A still further object of the present invention is to provide compounds, and compositions containing these compounds, which have high efficacy, low toxicity (such as low gastrointestinal irritability), prolonged duration of action, and/or good therapeutic indices.

These and other objects will become readily apparent from the detailed description which follows.

SUMMARY OF THE INVENTION

The present invention relates to specifically-substituted phenyl compounds, preferably substituted 2,6-di-tert-butyl phenol compounds, which are effective as anti-inflammatory agents, analgesic agents, antipyretic agents, antioxidant agents, anti-arthritic agents, and/or immunomodulating agents. These phenyl compounds are substituted with a low molecular weight alkyl chain which terminates in a specific unsaturated functional group. These unsaturated functionalities are —C≡CH, C═CH$_2$, C═C═CH$_2$, and aldehydes in the form of their acetals.

The present invention further relates to pharmaceutical compositions. These compositions comprise a compound of the present invention and a pharmaceutically-acceptable carrier.

Finally, the present invention also relates to methods for treating diseases characterized by inflammation, such as rheumatoid arthritis and osteoarthritis, in humans or lower animals. Such methods comprise administering to a human or lower animal in need of such treatment a safe and effective amount of a compound or composition of the present invention.

DETAILED DESCRIPTION OF THE INVENTION

Anti-inflammatory Agents

The compounds useful in the present invention are specifically-substituted phenyl compounds. Preferably, the compounds of the present invention are phenol compounds substituted in the 2 and 6 positions, independently, with a t-butyl, trimethylsilyl or trifluoromethyl group; and substituted in the 4 position with a specific low-molecular-weight alkyl chain which terminates in a specific unsaturated functional group. The terminal functionality is selected from —C≡CH, C═CH$_2$, C═C═CH$_2$, or aldehydes in the form of their acetals. Preferred are the —C≡CH and acetal terminal functionalities.

Specifically, the compounds of the present invention have the general structure:

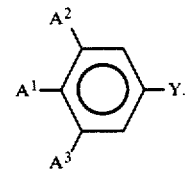

In this structure, A$^1$ is selected from the group consisting of —OH, —H, and —O$_2$CR; and wherein R is a straight or branched chain alkyl group having from 1 to about 10 carbon atoms, preferably methyl or ethyl. Preferred A$^1$ is —OH or —H, and most preferred A$^1$ is OH.

Furthermore, A$^2$ and A$^3$ are independently selected from the group consisting of —C(CH$_3$)$_3$, —Si(CH$_3$)$_3$, and —CF$_3$. It is preferred that A$^2$ and A$^3$ are the same group. Most preferred is A$^2$ and A$^3$ both being —C(CH$_3$)$_3$.

Thus, the generally most preferred compounds of the present invention have the general structure:

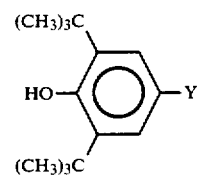

Finally, Y is a terminally unsaturated group selected from the group consisting of:

1. —(CR$^1$$_2$)$_n$—C≡C—H, wherein n is an integer from 1 to about 6;
2.

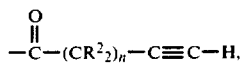

wherein n is an integer from 0 to about 5;

3.

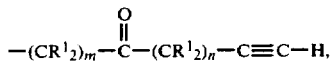

wherein m is an integer from 1 to about 5, and m+n is an integer from 1 to about 5; preferred is m=2;

4.

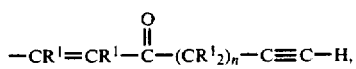

wherein n is 0 to 1;

5. $-(CR^1{}_2)_n-CR^3=CH_2$, wherein n is an integer from about 2 to about 6;

6.

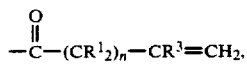

wherein n in an integer from 0 to about 5;

7.

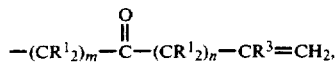

wherein m is an integer from 1 to about 3, and m+n is an integer from 1 to about 3; preferred is m=2;

8.

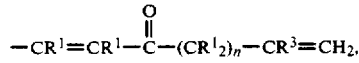

wherein n is an integer from 0 to about 3;

9. $-(CR^1{}_2)_n-CR^3=C=CH_2$, wherein n is an integer from 0 to about 6;

10.

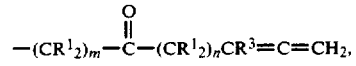

wherein m+n is an integer from 0 to about 5; preferred is m=0 or 2;

11.

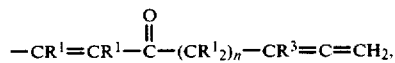

wherein n is an integer from 0 to about 3;

12. $-(CR^1{}_2)_n-CH(ZR^4)_2$, wherein n is an integer from 1 to about 6; and

13.

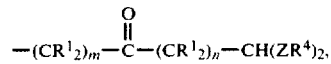

wherein n is an integer from 1 to about 5, m is an integer from 0 to about 4, and m+n is an integer from about 1 to about 5; preferred is m=0 or 2.

In these substituted Y groups, each $R^1$ is independently selected from the group consisting of —H, —OR$^3$, —NR$^3{}_2$, —NR$^3{}_3{}^+$, —N(R$^3$)C(O)R$^3$, —O$_2$CR$^3$, —CO$_2$R$^3$, —C(O)NR$^3{}_2$, straight or branched chain saturated alkyl group having from 1 to about 3 carbon atoms, and straight or branched chain unsaturated alkyl group having from 1 to about 3 carbon atoms. Preferably, $R^1$ is H, OH, =CH$_2$, methyl, or ethyl, and further preferred is no more than about two $R^1$ groups being other than H. Most preferred is all $R^1$ groups being H.

Each $R^2$ is independently selected from the group consisting of H, —OR$^3$, —NR$^3{}_2$, —NR$^3{}_3{}^+$, —N(R$^3$)C(O)R$^3$, —O$_2$CR$^3$, —CO$_2$R$^3$, —C(O)NR$^3{}_2$, straight or branched chain saturated alkyl group having from 1 to about 3 carbon atoms, and straight or branched chain unsaturated alkyl group having from 1 to about 2 carbon atoms. Preferably, $R^2$ is H, OH, =CH$_2$, methyl, or ethyl, and further preferred is no more than about two $R^2$ groups being other than H. Most preferred is all $R^2$ groups being H.

Each $R^3$ is independently selected from the group consisting of —H, methyl and ethyl. Preferably $R^3$ is —H.

Each $R^4$ is independently selected from the group consisting of —CH$_3$ and —CH$_2$CH$_3$, or the $R^4$'s may be joined to form a cyclic acetal such that both $R^4$'s together are one group selected from —(CH$_2$)$_2$— and —(CH$_2$)$_3$—. Preferred is both $R^4$ groups being methyl, or both $R^4$ groups together being —CH$_2$CH$_2$—. Most preferred is both $R^4$ groups being methyl.

Each Z is independently selected from the group consisting of O, S, NH, and NR$^4$. Preferred is Z being O or S, and most preferred is both Z groups being the same atom selected from O or S.

Specifically preferred acetal groups (i.e., —CH(ZR$^4$)$_2$ groups) are

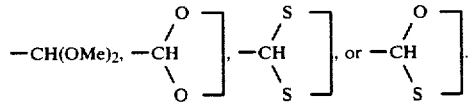

Most preferred specific acetals are

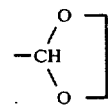

and, especially, —CH(OMe)$_2$.

Preferred Y groups are those having terminal —C≡CH or acetal functionalities:

1. $-(CR^1{}_2)_n-C\equiv CH$, wherein n is an integer from 1 to about 6;

2.

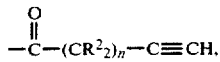

wherein n is an integer from 0 to about 5;
3.

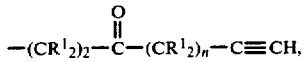

wherein n is an integer from 0 to about 3;
4.

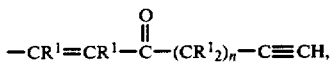

wherein n is 0 or 1;
5. $-(CR^1{}_2)_n-CH(ZR^4)_2$, wherein n is an integer from 1 to about 6;
6.

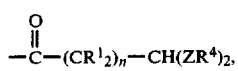

wherein n is an integer from 1 to about 5; and
7.

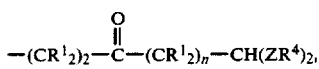

wherein n is an integer from 1 to about 3.
Most preferred Y groups are:
1.

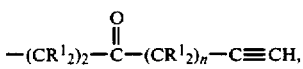

wherein n is an integer from 0 to about 3;
2.

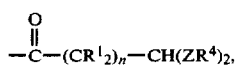

wherein n is an integer from 1 to about 5; and, especially,
3.

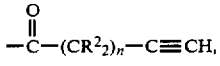

wherein n is an integer from 0 to about 5.

The compounds of the present invention include their pharmaceutically-acceptable salts. The term "pharmaceutically-acceptable salts", as used herein, means the compounds in their salt form which have the same general pharmacological properties as the protonated form from which they are derived, and which are acceptable from a toxicity viewpoint. Pharmaceutically-acceptable salts include alkali metal (e.g., sodium and potassium), alkaline earth metal (e.g., calcium and magnesium), non-toxic heavy metal (e.g., stannous and indium), and ammonium and low molecular weight substituted ammonium (mono-, di- and tri-methyl or ethyl ammonium) salts. Preferred are the sodium, potassium, and ammonium salts.

Compounds of the present invention include, for example,
1. 4-propynoyl-2,6-di-t-butylphenol;
2. 4-(1'-hydroxy-2'-propynyl)-2,6-di-t-butylphenol;
3. 4-(3'-butynoyl)-2,6-di-t-butylphenol;
4. 4-butadienoyl-2,6-di-t-butylphenol;
5. 4-(4'-pentynoyl)-2,6-di-t-butylphenol;
6. 4-(4'-pentenoyl)-2,6-di-t-butylphenol;
7. 4-(2'-dimethoxymethyl-4'-pentynoyl)-2,6-di-t-butylphenol;
8. 4-(2',2'-dimethyl-4'-pentynoyl)-2,6-di-t-butylphenol;
9. 4-(3',3'-dimethyl-4'-pentynoyl)-2,6-di-t-butylphenol;
10. 4-(4'-pentyn-3'-one)-2,6-di-t-butylphenol;
11. 4-(5'-hexynoyl)-2,6-di-t-butylphenol;
12. 4-(5'-hexenoyl)-2,6-di-t-butylphenol;
13. 4-(2'-methyl-5'-hexynoyl)-2,6-di-t-butylphenol;
14. 4-(1'-hydroxy-5'-hexynyl)-2,6-di-t-butylphenol;
15. 4-(5'-hexynyl)-2,6-di-t-butylphenol;
16. 4-(1'-methylidene-5'-hexynyl)-2,6-di-t-butylphenol;
17. 4-((S)-(−)-3'-methyl-5'-hexynoyl)-2,6-di-t-butylphenol;
18. 4-((R)-(+)-3'-methyl-5'-hexynoyl)-2,6-di-t-butylphenol;
19. 1-(5'-hexynoyl)-3,5-di-t-butylbenzene;
20. 4-(5'-hexynoyl)-2,6-bis-trimethylsilylphenol;
21. 1-(5'-hexynoyl)-3,5-bis-trimethylsilylbenzene;
22. 1-(5'-hexynoyl)-3,5-bis(trifluoromethyl)benzene;
23. 4-(6'-heptynoyl)-2,6-di-t-butylphenol;
24. 4-(6'-heptyn-3'-one)-2,6-di-t-butylphenol;
25. 4-(4'-(2''-propynyl)-6'-heptyn-3'-one)-2,6-di-t-butylphenol;
26. 4-(7'-octynoyl)-2,6-di-t-butylphenol;
27. 4-((E)-1'-penten-4'-yn-3'-one)-2,6-di-t-butylphenol;
28. 4-((E)-1',6'-heptadiene-3'-one)-2,6-di-t-butylphenol;
29. 4-(3',3'-dimethoxypropionyl)-2,6-di-t-butylphenol;
30. 4-(2'-(1'',3''-dioxolane)acetyl)-2,6-di-t-butylphenol;
31. 4-(3',3'-diethoxypropionyl)-2,6-di-t-butylphenol;
32. 4-(2'-(1'',3''-oxathiolane)acetyl)-2,6-di-t-butylphenol;
33. 4-(2',2'-dimethoxyethyl)-2,6-di-t-butylphenol;
34. 4-(5',5'-dimethoxy-3'-pentanone)-2,6-di-t-butylphenol; and
35. 4-(3',3'-dimethyl-5'-hexynoyl)-2,6-di-t-butylphenol.

Hereinafter, the above-noted compounds of the present invention may be referred to by the number preceding the name (i.e., "Compound 11" designates 4-(5'-hexynoyl)-2,6-di-t-butylphenol). Preferred compounds of the present invention are Compounds No. 4, 5, 6, 10, 11, 12, 13, 14, 17, 18, 23, 27, and 29. More preferred compounds are Compounds No. 10, 11, 17, 18, and 29. Most preferred is Compound No. 11.

The compounds of the present invention have utility as anti-inflammatory agents, analgesic agents, antipyretic agents, antioxidant agents, antiarthritic agents, antilipidemic agents, and/or immunomodulating agents. Furthermore, the phenolic compounds of the present invention may be useful as antioxidants for various non-pharmaceutical uses.

In order to determine and assess pharmacological activity, testing of these compounds in animals is carried out using various assays known to those skilled in the art. Thus, the anti-inflammatory activity of the compounds can be conveniently demonstrated using an assay designed to test the ability of these compounds to antagonize the local edema which is characteristic of the inflammatory response. Examples of such known tests include the carrageenan rat edema test, the oxazolone-induced inflamed mouse ear test, and the arachidonic acid-induced inflamed mouse ear test. Antipyretic acitivity may be tested using art-known rat models, and analgesic acitivty may be tested in art-known models such as the acetylcholine model in mice, the Randall-Selitto model in rats, and the hot-plate test in mice. Another useful art-known test is the adjuvant arthritis test which is a useful model for assessing anti-inflammatory activity and anti-resorptive activity in a chronic, rather than acute, model.

These and other appropriate tests for pharmacological activity are disclosed and/or referred to in U.S. Pat. No. 4,130,666, issued Dec. 19, 1978 to Moore; U.S. Pat. No. 4,440,784, issued Apr. 3, 1984 to Katsumi et al.; Japanese patent application No. 85/54315, published Mar. 28, 1985 by Katsumi et al.; European Patent Application Publication No. 59,090, published Sept. 1, 1982 by Yamanouchi Pharmaceutical Co., Ltd.; "Prostaglandin and Leukotriene Synthesis in Mouse Ears Inflamed by Arachidonic Acid", *The Journal of Investigative Dermatology*, 84, pp. 253-256 (1985); U.S. Pat. No. 4,431,656, issued Feb. 14, 1984, to Katsumi et al.; "Anti-inflammatory Activity of Anti-oxidants", by K. F. Swingle, et al., Chapter 4 of *Anti-inflammatory and Anti-rheumatic Drugs*, Vol. III (K. D. Rainsford, Editor; CRC Press, Inc., 1985); Adamkiewicz et al., *Canad. J. Biochem. Physio.;* 33; 332 (1955); Selye, *Brit. Med. J.;* 2; 1129 (1949); and Winter, *Proc. Exper. Biol. Med.;* 111; 554 (1962); the disclosures of all these patents and articles being incorporated herein by reference. Certain of these tests for pharmacological activity are also described in more detail in the Examples provided hereinafter.

The compounds of the present invention are prepared from commercially-available materials. Synthesis techniques useful for the preparation of the present compounds are described, for example, in U.S. Pat. Nos. 4,130,666 and 4,440,784, and in Japanese patent application No. 85/54315, as well as in several other of the patents and articles incorporated hereinbefore by reference. Representative procedures for synthesizing compounds of the present invention are provided in the Examples hereinafter.

The compounds of the present invention typically comprise from about 0.1% to about 99.9% by weight of the pharmaceutical compositions of the present invention, preferably from about 20% to about 80%, and most preferably from about 60% to about 80%.

As demonstrated by the animal test results provided in the Examples hereinafter, the compounds of the present invention are effective anti-inflammatory agents. Many of the compounds further surprisingly show anti-inflammatory activity at very low dosage levels. In addition, the compounds of the present invention have demonstrated surprisingly low toxicity, including very little gastrointestinal irritation even when dosed at levels well above dosage levels effective as anti-inflammatory agents. Thus, the compounds of the present invention have demonstrated very good therapeutic indices. Furthermore, the compounds of the present invention appear to have prolonged duration of action. This should permit less frequent dosing for the compounds of the present invention relative to the typical dosing every 4 hours for most commercially-available anti-inflammatory drugs.

The most preferred compound of the present invention, Compound 11 [i.e.: 4-(5'-hexynoyl)-2,6-di-t-butylphenol], has demonstrated very good oral activity in several animal models of inflammation as described in the Examples provided hereinafter. This compound is a dual inhibitor of the cyclooxygenase ("COX") and lipoxygenase ("LOX") enzymes in arachidonic acid metabolism, and hence has a mechanism distinct from classical NSAI drugs which only inhibit COX. In addition, Compound 11 has the following beneficial properties: antioxidant and free radical scavenging activity; very low or no gastric damage after oral dosing at levels significantly greater than the therapeutic dose in test animals; very low acute oral toxicity in test animals; oral analgesic activity (of the "peripheral" type, unlike opiate analgesia) superior to aspirin; ora anti-arthritic activity in a rat adjuvant arthritis model when dosed therapeutically; oral anti-pyretic activity; duration of action which may permit once- or twice-a-day dosing; the ability to decrease bone resorption in arthritic animal models; potential to alter pathological bone modeling and remodeling; potential to modulate the abnormal immune response associated with the arthritic condition; and potential to decrease tissue destruction in arthritic joints resulting from enzymatic attack.

Pharmaceutically-acceptable Carrier

In addition to the anti-inflammatory agent as described hereinbefore, the pharmaceutical compositions of the present invention essentially contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, mean that the components of the pharmaceutical composition are capable of being commingled with the anti-inflammatory agent, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as cornstarch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present. Other compatible pharmaceutical additives and actives (e.g., other NSAI drugs; pain killers; muscle relaxants) may be included in the pharmaceutically-acceptable carrier for use in the compositions of the present invention.

The choice of a pharmaceutically-acceptable carrier to be used in conjunction with the anti-inflammatory agents of the present composition is basically determined by the way the compound is to be administered. If the compound is to be injected, the preferred pharmaceutically-acceptable carrier is sterile, physiological saline, with blood compatable suspending agent, the pH of which has been adjusted to about 7.4. Suitable Pharmaceutically-acceptable carriers for topical application include those suited for use in creams, gels, tapes and the like.

The preferred mode of administering the compounds of the present invention is orally. The preferred unit dosage form is therefore tablets, capsules and the like, comprising a safe and effective amount of the anti-inflammatory compound of the present invention, which is preferably from about 10 mg to about 3500 mg, more preferably from about 25 mg to about 1000 mg, and most preferably from about 50 mg to about 600 mg. Pharmaceutically-acceptable carriers suitable for the preparation of unit dosage forms for oral administration are well-known in the art. Their selection will depend on secondary considerations like taste, cost, shelf stability, which are not critical for the purposes of the present invention, and can be made without difficulty by a person skilled in the art.

The pharmaceutically-acceptable carrier employed in conjunction with the anti-inflammatory agents of the present invention is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 20% to about 80%, and most preferably from about 20% to about 40%.

Method for Treating Diseases Characterized by Inflammation

Another aspect of the present invention is methods for treating diseases characterized by inflammation. Such methods comprise administering to a human or lower animal in need of such treatment a safe and effective amount of an anti-inflammatory agent described hereinbefore.

The preferred mode of administration is oral, but other known methods of administration are contemplated as well, e.g., dermatomucosally (for example, dermally, rectally and the like) and parenterally (for example, by subcutaneous injection, intra-muscular injection, intra-articular injection, intravenous injection and the like). Ocular administration and inhalation is also included. Thus, specific modes of administration include, without limitation, oral, transdermal, mucosal, sublingual, intramuscular, intravenous, intraperitoneal, and subcutaneous administration, as well as topical application.

The term "diseases characterized by inflammation", as used herein, means conditions which are known to involve inflammation, such as arthritis (e.g., rheumatoid arthritis; osteoarthritis; psoriatic arthritis; juvenile arthritis; Reiter's syndrome; infectous arthritis; ankylosing spondylitis; systemic lupus erythematosus; and gout), as well as the presence of inflammation whether or not it is associated with an identifiable disease. Diseases characterized by inflammation further include inflammation of the gastrointestinal tract, including the oral cavity (e.g., inflammation associated with gingivitis or periodontal disease) and bowels (e.g., inflammation associated with inflammatory Bowl Disease); inflammation associated with dermatological diseases (e.g., psoriosis): and inflammation associated with the respiratory tract (e.g. pulmonary inflammation).

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of the anti-inflammatory agent will vary with the particular condition being treated, the age and physical condition of the patient being treated, the severity of the condition, the duration of the treatment, the nature of concurrent therapy, the specific anti-inflammatory agent employed, the particular pharmaceutically-acceptable carrier utilized, and like factors within the knowledge and expertise of the attending physician. However, single dosages can range from about 10 mg to about 3500 mg, or from about 0.2 mg/kg of body weight to about 70 mg/kg of body weight. Preferred single dosages are from about 50 mg to about 600 mg, or from about 1 to about 12 mg/kg of body weight. Up to about 6 single dosages per day may be administered.

The following Examples further describe and demonstrate the preferred embodiments within the scope of the present invention. The Examples are given solely for the purpose of illustration, and are not to be construed as limitations of the present invention since many variations thereof are possible without departing from its spirit and scope. All temperature readings are in °C.

EXAMPLE 1

Synthesis of 4-(5'-hexynoyl)-2,6-di-tert-butylphenol

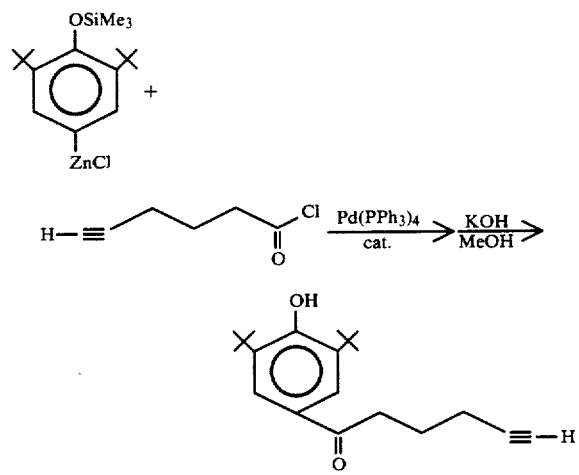

A mixture of 0.24 g (10 mmol) of magnesium, 2.14 g (6.00 mmol) of 2,6-di-t-butyl-4-bromo-1-trimethylsiloxybenzene [which is prepared from di-t-butylphenol by sequential reactions with bromine (CH₂Cl₂, 0°C., 15 min) and n-butyllithium (THF, −78° C., 15 min)/-chlorotrimethylsilane (−78→25° C., 18 h)] and a few drops of 1,2-dibromoethane in 25 ml of THF is heated at reflux for two hours and then is added at 0° to a mixture of 1.09 g (8.00 mmol) of zinc chloride in 25 mL of THF. The resulting slurry is stirred at room temperature for 15 minutes and then is treated successively with 0.30 g (5 mol %) of tetrakis(triphenylposphine)palladium and 5.0 mmol of 5-hexynoyl chloride [which is prepared by the sequential treatment of 5-hexynoic acid in ether with n-butyllithium (5.0 mmol, 0°→RT) and oxalyl chloride (5.0 mmol, RT→40°, the resulting acid chloride is used in situ)]. After stirring at room temperature for one hour, the mixture is poured into sat. NH₄Cl. The layers are separated and the aqueous portion is extracted with pentane. The combined organic phase is washed with sat. NaCl and dried (MgSO₄). The crude, concentrated ketone is then diluted with 25 mL each of methanol and THF, and is then treated at 25° with 5 mL of 1N KOH. After stirring for one hour the mixture is poured into 1N HCl. The aqueous portion is extracted with pentane and the combined organic phase is washed with sat. NaCl and dried (MgSO₄). The concentrate is purified by flash chromatography (silica gel, 5% EtOAc/hexane, $R_f$=0.26) to provide 0.78 g (52%) of the title compound: mp 62°–63°; IR (CCl₄) 3640(s), 3320(m), 2960(s), 2120(w), 1675(s), 1320(m), 1160(m), 630(m) cm⁻¹; ¹H-NMR (CDCl₃)δ(ppm) 1.45(s, 18H), 1.8–2.4(m, 5H), 2.95(t, 2H), 5.60(s, 1H), 7.70(s, 2H); ¹³C-NMR (CDCl₃)δ17.98. 23.35, 30.15, 34.39, 36.47, 69.07, 83.90, 125.78, 128.81, 135.83, 158.41, 198.95 ppm.

EXAMPLE 2

Synthesis of 4-(5'-hexenoyl)-2,6-di-tert-butylphenol

In a manner similar to that described hereinbefore in Example 1, 0.88 g (7.8 mmol) of 5-hexenoic acid is converted into the corresponding acid chloride, coupled with the aryl zinc reagent, and then desilyated to afford, after chromatography (5% EtOAc/hexane, $R_f$=0.21) and recrystallization (hexane), 0.52 g (22%) of the title compound: mp 72°–73°; IR (CCl₄) 3630(s), 2950(s), 1670(s), 1585(m), 910(m) cm⁻¹; ¹H-NMR (CDCl₃)δ(ppm) 1.40(s, 18H), 1.6–2.1(m, 4H), 2.80(t, 2H), 4.7–5.1(m, 2H), 5.3–6.1(m, 1H), 5.60(s, 1H), 7.75(s, 2H); ¹³C-NMR (CDCl₃)δ23.85, 30.16, 33.33, 34.37, 37.18, 115.15, 125.78, 128.96, 135.79, 138.17, 158.32, 199.47 ppm.

EXAMPLE 3

Synthesis of 4-(4'-pentynoyl)-2,6-di-tert-butylphenol

Following the general procedure described hereinbefore in Example 1, 0.98 g (10.0 mmol) of 4-pentynoic acid is converted into the corresponding acid chloride, coupled with the aryl zinc reagent, and then desilyated to afford, after chromatography (5% EtOAc/hexane, $R_f$=0.17) and recrystallization (hexane), 0.64 g (22%) of the title compound: mp 100°–101°; IR (CCl₄) 3620(s), 3300(m), 2950(s), 2110(w), 1665(s), 1190(s) cm⁻¹; ¹H-NMR (CDCl₃)δ(ppm) 1.45(s, 18H), 1.90(t, 1H), 2.3–2.8(m, 2H), 2.9–3.3(m, 2H), 5.65(s, 1H), 7.75(s, 2H); ¹³C-NMR (CDCl₃)δ13.44, 30.15, 34.38, 37.02, 68.60, 83.75, 125.78, 128.42, 135.87, 158.57, 196.84 ppm.

EXAMPLE 4

Synthesis of 4-(2'-methyl-5'-hexynoyl)-2,6-di-tert-butylphenol

In a procedure similar to that described hereinbefore in Example 1, 1.23 g (9.75 mmol) of 2-methyl-5-hexynoic acid (which is prepared from 5-hexynoic acid by the sequence: silylation of the triple bond using LDA/-chlorotrimethylsilane, alkylation using LDA/methyl iodide, and desilylation using KF.2H₂O/DMF) is converted into the corresponding acid chloride, coupled with the aryl zinc reagent, and then desilylated to afford, after chromatography (5% EtOAc/hexane, $R_f$=0.23), 0.76 g (25%) of the title compound: IR (CDCl₃) 3620(s), 3300(m), 2960(s), 2110(w), 1660(s), 1580(m), 1210(s), 630(m) cm⁻¹; ¹H-NMR (CDCl₃)δ(ppm) 1.15(d, 3H), 1.40(s, 18H), 1.7–2.2(m, 4H), 3.4(m, 1H), 5.50(s, 1H), 7.65(s, 2H); ¹³C-NMR (CDCl₃)δ16.39, 17.29, 30.19, 32.32, 34.44, 38.33, 69.00, 83.93, 126.23, 128.20, 135.87, 158.50, 203.25 ppm.

EXAMPLE 5

Synthesis of 4-(4'-pentenoyl)-2,6-di-tert-butylphenol

Following the representative procedure described hereinbefore in Example 1, 1.00 g (10.0 mmol) of 4-pentenoic acid is converted into the corresponding acid chloride, coupled with the aryl zinc reagent, and then desilylated to afford, after chromatography (5% EtOAc/hexane, $R_f$=0.25), 1.51 g (52%) of the title compound. Recrystallization from hexane provides 0.71 g of the product; mp 89°–90°; IR (CHCl₃) 3630(s), 2960(s), 1665(s), 1585(m), 1160(s), 995(w), 915(s) cm⁻¹; ¹H-NMR (CDCl₃)δ(ppm) 1.40(s, 18H), 2.35(t, 2H), 2.7–3.0(m, 2H) 4.6–5.0(m, 2H), 5.3–5.9(m, 1H), 5.50(s, 1H), 7.60(s, 2H); ¹³C-NMR (CDCl₃)δ(off-resonance multiplicity) 28.58(t), 30.16(q), 34.42(s), 37.37(t), 115.10(t), 125.75(d), 128.89(s), 135.85(s), 137.71(d), 158.34(s), 198.61(s) ppm.

EXAMPLE 6

Synthesis of 4-[(S)-(−)-3'-methyl-5'-hexynoyl]-2,6-di-tert-butylphenol

In a manner similar to the general procedure described hereinbefore in Example 1, 1.03 g (8.20 mmol) of S-(−)-3-methyl-5-hexynoic acid ($[\alpha]_D^{25}$=−11.80°, ether; which is prepared from R-(−)-methyl 3-hydroxy-2-methylpropionate by the sequence: protection as the THP ether, reduction with LiAlH₄, conversion of the alcohol to the tosylate and then to the bromide, treatment with lithium acetylide-EDA in DMSO, silylation of the acetylene, deprotection of the THP-protected alcohol, conversion of the alcohol to the tosylate and then to the nitrile, and hydrolysis of the nitrile using KOH) is converted into the corresponding acid chloride, coupled with the aryl zinc reagent, and then desilylated to afford, after chromatography (5% EtOAc/hexane, $R_f$=0.20) and recrystallization (heptane), 0.761 g (30%) of the title compound: $[\alpha]_D^{25}$=−11.7°; mp 67°–68.5°; IR (CDCl₃) 3630(s), 3310(s), 2950(s), 2110(w), 1660(s), 1590(s), 1425(s), 1310(s), 1245(s), 1210(s) cm⁻¹; ¹H-NMR (CDCl₃)δ(ppm) 1.0–1.2(m, 4H), 1.40(s, 18H), 1.90(t, 1H), 2.0–3.0(m, 4H), 5.65(s, 1H), 7.70(s, 2H); ¹³C-NMR (CDCl₃)δ(off-resonance multiplicity) 19.75 (q), 25.61(t), 29.17(d), 30.15(q), 34.39(s), 43.63(t), 70.02(d), 82.56(s), 125.90(d), 129.03(s), 135.83(s), 158.44(s), 198.78(s) ppm.

EXAMPLE 7

Synthesis of 4-[(R)-(−)-3′-methyl-5′-hexynoyl]-2,6-di-tert-butylphenol

Following the general procedure described hereinbefore in Example 1, 1.03 g (8.20 mmol) of R-(+)-3-methyl-5-hexynoic acid ($[α]_D^{26} = +11.90°$, ether; which is prepared from S-(+)-methyl 3-hydroxy-2-methylpropionate by the sequence essentially the same as in Example 6 hereinbefore for the stereoisomer) is converted into the corresponding acid chloride, coupled with the aryl zinc reagent, and then desilylated to afford, after chromatography (5% EtOAc/hexane, $R_f$=0.20) and recrystallization (heptane), 0.752 g (29%) of the title compound: $[α]_D^{26} = +12.2°$; mp 67°–68.5°; IR (CDCl₃) 3630(s), 3310(m), 2950(s), 2110(w), 1660(s), 15901425(s), (s), 1310(s), 1245(s), 1210(s) cm⁻¹; ¹H-NMR (CDCl₃)δ(ppm) 1.0–1.2(m, 4H), 1.40(s, 18H), 1.90(t, 1H), 2.0–3.0(m, 4H), 5.65(s, 1H), 7.70(s, 2H); ¹³C-NMR (CDCl₃)δ(off resonance multiplicity) 19.75(q), 25.61(t), 29.17(d), 30.15(q), 34.39(s), 43.63(t), 70.02(d), 82.56(s), 125.90(d), 129.03(s), 135.83(s), 158.44(s)198.78(s) ppm.

EXAMPLE 8

Synthesis of 1-(5′-hexynoyl)-3,5-di-tert-butylbenzene

A mixture of 0.73 g (30 mmol) of magnesium, 4.04 g (15.0 mmol) of 1-bromo-3,5-di-t-butylbenzene (which is prepared from the bromination of 1,3,5-tri-t-butylbenzene with Br₂/Fe) and a few drops of 1,2-dibromoethane in 25 mL of THF is heated at reflux for two hours and then is added at 0° to a mixture of 2.73 g (20.0 mmol) of zinc chloride in 40 mL of THF. The resulting slurry is stirred at room temperature for 15 minutes and then is treated successively with 0.70 g (5 mol%) of tetrakis(triphenylphosphine)palladium and 1.56 g (12.0 mmol) of 5-hexynoyl chloride. After stirring at room temperature for two hours the mixture is poured into sat. NH₄Cl. The layers are separated and the aqueous portion is extracted with pentane. The combined organic phase is washed with sat. NaCl and dried (MgSO₄). The concentrate is purified by flash chromatography (silica gel, 2% EtOAc/hexane, $R_f$=0.19) to provide 2.58 g (75%) of the title compound: IR (neat) 3300(m), 2975(s), 2110(w), 1680(s), 1595(m), 1365(s), 1250(m), 1220(m), 705(s) cm⁻¹; ¹H-NMR (CDCl₃)δ(ppm) 1.25(s, 18H), 1.7–2.3(m, 5H), 2.90(t, 2H), 7.40(d, J=3 Hz; 1H), 7.60(d, J=3 Hz, 2H); ¹³C-NMR (CDCl₃) (off-resonance multiplicity)δ17.88(t), 23.13(t), 31.37(q), 34.91(s), 36.93(t), 69.25(d), 83.69(s), 122.25(d), 127.06(d), 136.78(s), 151.06(s), 199.69(s) ppm.

EXAMPLE 9

Synthesis of 4-(5′-hexynyl)-2,6-di-tert-butylphenol

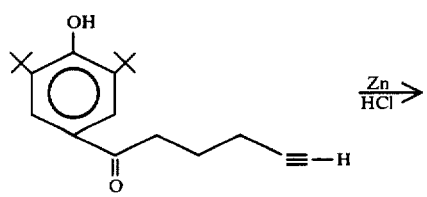

Zinc amalgam is prepared by treating 4.0 g (60 mmol) of granular zinc with enough 5% mercuric chloride solution to cover the metal completely. After standing for one hour, the liquid is decanted from the flask and to the reaction mixture is added a solution of 3.00 g (10.0 mmol) of 4-(5′-hexynoyl)-2,6-di-t-butylphenol (as in Example 1 hereinbefore) in 25 mL of ethanol followed by 2 mL of concentrated HCl. The mixture is refluxed for two hours and then is treated with an additional 2 mL of concentrated HCl. After refluxing overnight, the reaction solution is poured into 50 mL of 10% NaCl and extracted with ether. The combined organic phase is dried (MgSO₄) and purified by flash chromatography (5% EtOAc/hexane, $R_f$=0.63) and Kugelrohr distillation (oven temp 130°/0.04 torr) to afford 0.90 g (32%) of the title compound: IR (CHCl₃) 3640(s), 3310(m), 2955(s), 2110(w), 1430(s), 1160(m), 630(m), cm⁻¹; ¹H-NMR (CDCl₃)δ(ppm) 1.35(s, 18H), 1.4–2.6(m, 8H), 1.80(t, 1H), 4.90(s, 1H) 6.80(s, 2H); ¹³C-NMR (CDCl₃) δ18.28, 28.20, 30.35, 30.88, 34.20, 35.32, 68.21, 84.40, 124.68, 132.71, 135.58, 151.70 ppm.

EXAMPLE 10

Synthesis of 4-(1′-hydroxy-5′-hexynyl)-2,6-di-tert-butylphenol

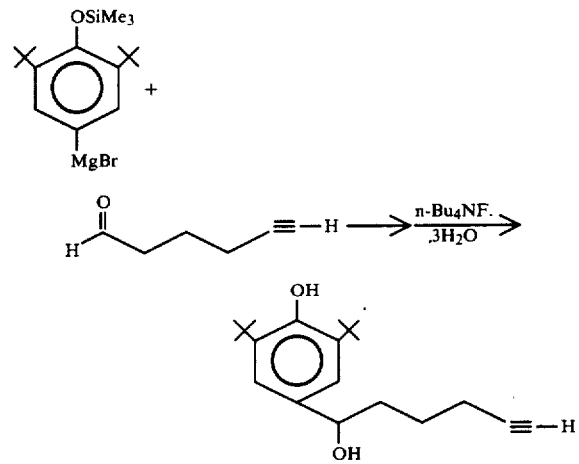

A mixture of 3.0 g (120 mmol) of magnesium, 25.7 g (72.0 mmol) of 2,6-di-t-butyl-4-bromo-1-trimethylsiloxybenzene and a few drops of 1,2-dibromoethane in 350 mL THF is heated at reflux for two hours and then is cooled to −78° and to it is added 5.78 g (60.0 mmol) of 5-hexynal (which is prepared from the oxidation of 5-hexyn-1-ol using pyridinium chlorochromate). The reaction mixture is stirred at −78° for 15 minutes and then is allowed to warm to 0°, where it is stirred for an additional 30 minutes. The mixture is poured into sat. NH₄Cl and the aqueous layer is extracted with pentane. The combined organic phase is washed with sat. NaCl and dried (MgSO₄). The crude silylated intermediate is concentrated, dissolved in 300 mL of THF, and treated at room temperature with 28.5 g (90.0 mmol) of tetra-n-butylammonium fluoride trihydrate. After stirring the mixture at 25° for one hour, it is poured into sat. NH₄Cl and the layers are separated. The aqueous portion is extracted with pentane and the combined organic phase is washed with sat. NaCl and then dried (MgSO₄). The concentrate is purified by flash chromatography (10% EtOAc/hexane, $R_f$=0.16) and recrystallization (hexane) to afford 5.38 g (30%) of the title compound: mp 70°-71°; IR (CCl₄) 3620(s), 3310(m), 2960(s), 1430(s), 1160(s), 630(m) cm⁻¹; ¹H-NMR (CDCl₃)δ(ppm) 1.40(s, 18H), 1.5-2.3(m, 8H), 4.50(t, 1H), 5.15(s, 1H), 7.10(s, 2H); ¹³C-NMR δ18.09, 24.88, 30.19, 34.22, 37.69, 68.51, 74.37, 84.25, 122.46, 135.16, 135.75, 153.04 ppm.

EXAMPLE 11

Synthesis of 4-(6'-heptynoyl)-2,6-di-tert-butylphenol

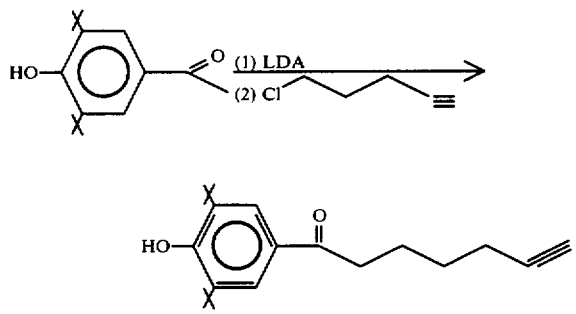

A solution of 2.24 mL (16.0 mmol) of diisopropylamine in 75 mL of THF is treated at −78° with 5.36 mL (15.0 mmol) of 2.80M n-butyllithium. The solution is warmed to 0° and stirred for an additional 15 minutes, then is cooled back to −78° and to it is added 1.80 g (7.25 mmol) of 4-acetyl-2,6-di-t-butylphenol (which is prepared from Friedel-Crafts acylation of 2,6-di-t-butylphenol using acetyl chloride and titanium tetrachloride). The reaction mixture is allowed to warm to 0° and stirred for 30 minutes. The viscous white slurry is then treated successively with 5.0 mL of HMPA and 0.83 g (8.0 mmol) of 5-chloro-1-pentyne and is then let warm to 25°, where it is stirred for one hour. The reaction mixture is poured into 1N HCl and the layers are separated. The aqueous portion is extracted with pentane and the combined organic phase is washed with 1N HCl, sat. NaHCO₃, sat. NaCl and then dried (MgSO₄). After removing residual 4-acetyl-2,6-di-t-butylphenol by crystallization with hexane, the concentrate is purified by flash chromatography (10% EtOAc/hexane, $R_f$=0.33) and recrystallization (heptane) to provide 0.422 g (19%) of the title compound: mp 76°-78°; IR (CDCl₃) 3630(s), 3310(m), 2960(s), 2110(w), 1665(s), 1585(m), 1215(s), 630(m) cm⁻¹; ¹H-NMR (CDCl₃)δ(ppm) 1.40(s, 18H), 1.5-2.0(m, 5H), 2.20(t, 2H), 2.85(t, 2H), 5.60(s, 1H), 7.70(s, 2H); ¹³C-NMR (CDCl₃)δ18.36, 23.79, 28.24, 30.19, 34.41, 37.50, 68.53, 84.21, 125.79, 128.89, 135.79, 158.34, 199.26 ppm

EXAMPLE 12

Synthesis of 4-propynoyl-2,6-di-tert-butylphenol

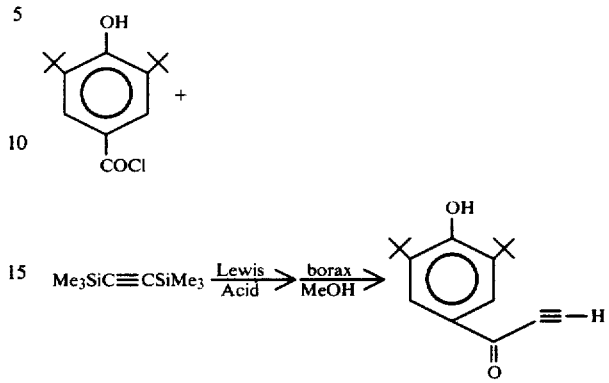

A solution of 3.40 g (20.0 mmol) of bis(trimethylsilyl)acetylene and 4.03 g (15.0 mmol) of 3,5-di-t-butyl-4-hydroxybenzoyl chloride [which is prepared from 3,5-di-t-butyl-4-hydroxybenzoic acid by treatment with oxalyl chloride (benzene, 60°, 2h)] in 80 mL of methylene chloride is treated at −78° with 1.78 mL (16.5 mmol) of titanium tetrachloride. The resulting dark mixture is stirred at −78° for 30 minutes and then is allowed to warm to 0° and stirred for an additional 30 minutes. The reaction solution is poured into 3N HCl and the layers are separated. The aqueous portion is extracted with pentane and the combined organic phase is washed with sat. NaCl and dried (MgSO₄). The crude silylacetylene intermediate is concentrated, dissolved in 100 mL of methanol and then is treated at room temperature with 20 mL of 0.01M borax. After stirring the mixture at 25° overnight, it is poured into 3N HCl and the aqueous layer is extracted with pentane. The combined organic phase is washed with sat. NaCl and dried (MgSO₄). Recyrstallization from hexane affords 2.40 g (62%) of the title compound: mp 100°-101°; IR (CCl₄) 3620(s), 3300(m), 2950(s), 2090(m), 1640(s), 1580(s), 1290(s), 1215(vs) cm⁻¹; ¹H-NMR (CDCl₃)δ(ppm) 1.45(s, 18H), 3.30(s, 1H), 5.80(s, 1H), 8.00(s, 2H); ¹³C-NMR (CDCl₃)δ30.09, 34.41, 79.84, 80.80, 127.76, 128.51, 136.34, 160.02, 176.67 ppm.

EXAMPLE 13

Synthesis of 4-[(E)-1'-penten-4'-yn-3'-one]-2,6-di-tert-butylphenol

After coupling (E)-3-(3',5'-di-t-butyl-4'-hydroxyphenyl)propenoyl chloride (which is prepared from the sequence: Wittig reaction of 3,5-di-t-butyl-4-hydroxybenzaldehyde with (Carboethoxymethylene)triphenylphosphorane, hydrolysis of the ester moiety, and reaction with oxalyl chloride) with bis(trimethylsilyl)acetylene to obtain the corresponding silylated alkyne in a manner similar to that described hereinbefore for Example 12, desilylation to liberate the terminal ynone is accomplished as follows. A solution of 1.25 g (3.5 mmol) of 4-[(E)-5'-trimethylsilyl-1'-penten-4'-yn-3'-one]-2,6-di-t-butylphenol in a mixture of 20 mL of THF and 30 mL of methanol is treated at room temperature with 10 mL of 0.01N borax and stirred for four hours. The reaction mixture is then poured into 1N HCl and the layers are separated. The aqueous portion is extracted with pentane and the combined organic phase is washed with sat. NaCl and dried (MgSO₄). The concentrate is purified by flash chromatography (10% EtOAc/hexane, R_f=0.20) to afford 0.80 g (80%) of the title compound: mp 101°-102°; IR (CHCl₃) 3620(s), 3300(m), 2950(s), 2090(m), 1615(s), 1580(s), 970(m) cm⁻¹; ¹H-NMR (CDCl₃)δ(ppm) 1.40(s, 18H), 3.10(s, 1H), 5.45(s, 1H), 6.45(d, J=16 Hz, 1H), 7.20(s, 2H), 7.60(d, J=16 Hz, 1H); ¹³C-NMR (CDCl₃)δ(off-resonance multiplicity) 29.96(q), 34.20(s), 78.70(d), 80.01(s), 125.11 (two carbon atoms, d and s), 126.26(d), 136.64(s), 151.16(d), 157.25(s), 177.41(s) ppm.

EXAMPLE 14

Synthesis of 4-(4'-pentyl-3'-one)-2,6-di-tert-butylphenol

After coupling 3-(3', 5'-di-t-butyl-4'-trimethylsiloxyphenyl)propionyl chloride (which is prepared from the sequence: reaction of the Grignard reagent derived from 2,6-di-t-butyl-4-bromo-1-trimethylsiloxybenzene with ethylene oxide, conversion of the alcohol moiety to the tosylate and then to the bromide, Grignard preparation followed by carbonation, and reaction with oxalyl chloride) with bis(trimethylsilyl)acetylene to obtain the corresponding silylated alkyne in a procedure similar to that described hereinbefore for Example 12, desilylation to liberate the terminal ynone is accomplished as follows. A solution of 27.1 g (63.0 mmol) of 4-(5'-trimethylsilyl-4'-pentyn-3-one)-2,6-di-t-butyl-1-trimethylsiloxybenzene in 200 mL of THF and 125 mL of methanol is treated at room temperature with 370 mL of 0.01M borax. After stirring for 90 minutes at 25°, the reaction mixture is poured into 1N HCl and the layers are separated. The aqueous portion is extracted with pentane and the combined organic phase is washed with sat. NaHCO₃ and sat. NaCl, and then dried (MgSO₄). The concentrate is purified by flash chromatography (3% EtOAc/hexane, R_f=0.15) to afford 14.5 g (80%) of the title compound which is further recrystallized from hexane: mp 52°-53°; IR (CDCl₃) 3640(s), 3300(m), 2960(s), 2090(s), 1675(s), 1435(s), 1100(m) cm⁻¹; ¹H-NMR (CDCl₃)δ(ppm) 1.45(s, 18H), 2.90(s, 4H), 3.15(s, 1H), 5.05(s, 1H), 7.00(s, 2H); ¹³C-NMR (CDCl₃) δ(off-resonance multiplicity) 29.65(t), 30.30(q), 34.29(s), 47.49(t), 78.64(d), 81.47(s), 124.79(d), 130.48(s), 136.03(s), 152.21(s), 186.51(s) ppm.

EXAMPLE 15

Synthesis of 4-(5'-hexynoyl)-2,6-bis-trimethylsilylphenol

A solution of 7.04 g (18.4 mmol) of 1-trimethylsiloxy-2,4,6-tris-trimethylsilylbenzene (which is prepared from 2,4,6-tribromophenol by silylation using imidazole/-chlorotrimethylsilane followed by reaction in refluxing THF with Mg/chlorotrimethylsilane) is treated successively at −78° with 2.65 g (20.3 mmol) of 5-hexynoyl chloride and 2.23 mL (20.7 mmol) of titanium tetrachloride. The mixture is stirred at −78° for three hours and is then poured into 1N HCl. The layers are separated and the aqueous portion is extracted with pentane. The combined organic phase is then washed with sat. NaCl and dried (MgSO₄). The crude, concentrated silyl ether is dissolved in a mixture of 100 mL of methanol and 130 mL of THF and is treated at room temperature with 100 mL of 0.01M borax. After stirring the mixture at 25° for one hour, the reaction mixture is poured into 1N HCl and the layers are separated. The aqueous portion is extracted with pentane and the combined organic phase is washed with sat. NaCl and dried (MgSO₄). The concentrate is purified by flash chromatography (silica gel, 5% EtOA/hexane containing 0.5% triethylamine, R_f=0.22) to afford 1.28 (21%) of the title compound: IR (CDCl₃) 3600(s), 3300(m), 2950(s), 2110(w), 1665(s), 1565(s), 1250(s), 840(s) cm⁻¹; ¹H-NMR (CDCl₃)δ(ppm) 0.20(s, 18H), 1.6-2.1(m, 5H), 2.70(t, 2H), 5.30(s, 1H), 7.70(s, 2H); ¹³C-NMR (CDCl₃) δ−0.81, 17.80, 23.14, 36.36, 68.96, 83.66, 124.19, 129.50, 137.44, 169.05, 198.65 ppm.

EXAMPLE 16

Synthesis of 4-(3',3'-dimethoxypropionyl)-2,6-di-tert-butylphenol

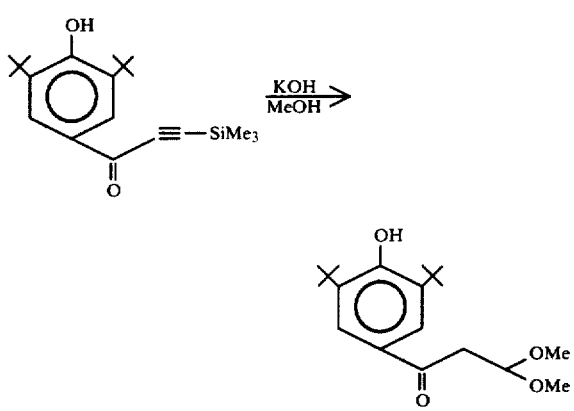

A solution of 11.5 g (35.0 mmol) of 4-trimethylsilylpropynoyl-2,6-di-t-butylphenol in 80 mL of THF and 200 mL of methanol is treated at room temperature with 200 mL of 1N KOH and the mixture is stirred overnight. The reaction is poured into 1N HCl and the layers are separated. The aqueous portion is extracted with ether and the combined organic phase is dried (MgSO₄). The concentrate is purified by flash chromatography (10% EtOAc/hexane, R_f=0.15) to afford 10.1 g (90%) of the title compound: IR (CDCl₃) 3620(s), 2950(s), 1660(s), 1580(m), 1320(s), 1115(s), 1050(s) cm⁻¹; ¹H-NMR (CDCl₃) δ(ppm) 1.40(s, 18H), 3.15 (d, J=5 Hz, 2H), 3.30(s, 6H), 4.85(t, J=5 Hz, 1H), 5.75(s, 1H), 7.75(s, 2H); ¹³C-NMR (CDCl₃)δ(off-resonance multiplicity) 30.11(q), 34.39(s), 42.26(t), 54.10(q), 102.69(d), 126.07(d), 128.94(s), 135.94(s), 158.66(s), 195.94(s) ppm.

EXAMPLE 17

Synthesis of 4-[2'-(1'',3''-dioxolane)acetyl]-2,6-di-tert-butylphenol

A mixture of 0.99 g (3.0 mmol) of 4-trimethylsilylropynoyl-2,6-di-t-butylphenol and 20 mL (360 mmol) of ethylene glycol in 20 mL of THF is treated at room temperature with 20 mL of 1N KOH and stirred for 24 hours. The reaction solution is poured into 0.5N HCl and the layers are separated. The aqueous portion is extracted with ether and the combined organic phase is dried (MgSO₄). Purification of the concentrate by flash chromatography (15% EtOAc/hexane, R_f=0.31) afforded 0.43 g (45%) of the title compound: mp 102°-103°; IR (CDCl₃) 3630, 2960, 2890, 1665, 1585, 1415, 1360, 1325, 1220, 1125, 1030 cm⁻¹; ¹H-NMR (CDCl₃)δ(ppm) 1.33(s, 18H), 3.10(d, 2H), 3.75(m, 4H), 5.23(t, 1H), 5.57(s, 1H), 7.63(s, 2H).

EXAMPLE 18

Synthesis of 4-(3'-butynoyl)-2,6-di-tert-butylphenol

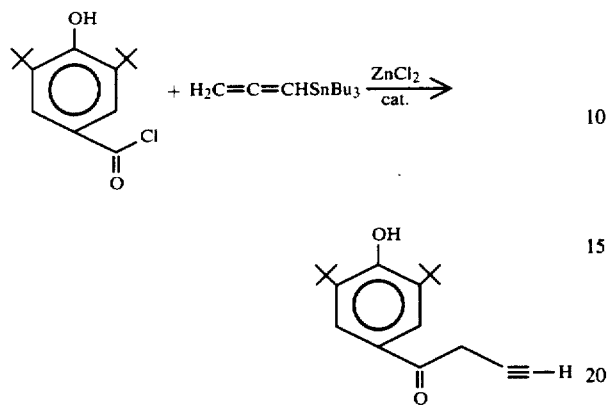

A solution of 3.76 g (14.0 mmol) of 3,5-di-t-butyl-4-hydroxybenzoyl chloride in 35 mL of benzene is treated successively at 0° with 3.68 g (11.2 mmol) of allenyl-tributyltin (which is prepared from reaction of the Grignard reagent derived from propargyl bromide with tri-n-butyltin chloride) and 0.05 g (0.4 mmol) of zinc chloride. The mixture is stirred at 0° for 20 minutes and then at room temperature for 30 minutes. A small amount (1-2 mL) of formic acid is added to the reaction mixture and it is then concentrated. Purification by flash chromatography (10% ether/pet. ether containing 0.5% formic acid, $R_f$=0.27) and recrystallization (hexane containing 0.5% formic acid) affords 0.572 g (19%) of the title compound, which contains about 10% of the isomeric 4-butadienoyl-2,6-di-t-butylphenol: mp 94°–96°; IR (CCl$_4$) 3640(s), 3310(m), 2960(s), 2110(w), 1680(s), 1585(m), 1305(s), 1235(s) cm$^{-1}$; $^1$H-NMR (CDCl$_3$)δ(ppm) 1.40(s, 18H), 2.15(t, J=3 Hz, 1H), 3.65(d, J=3 Hz, 1H), 5.65(s, 1H), 7.70(s, 2H); $^{13}$C-NMR (CDCl$_3$)δ30.09, 34.35, 73.05, 78.41, 93.23, 126.55 (two carbons?), 135.88, 158.89, 191.88 ppm.

EXAMPLE 19

Synthesis of 4-butadienoyl-2,6-di-tert-butylphenol

A mixture of 0.20 g (0.75 mmol) of 4-(3'-butynoyl)-2,6di-t-butylphenol in 1 mL each of sat. NaHCO$_3$ and THF is stirred overnight at room temperature and is then poured into water. The layers are separated and the aqueous portion is extracted with pentane. The combined organic phase is washed with sat. NaCl and dried (MgSO$_4$). Recrystallization (hexane) provides 0.147 (74%) of the title compound: mp 100°–102°; IR (CCl$_4$) 3640(s), 3510(m), 2960(s), 1965(m), 1935(m), 1645(s), 1585(m), 1305(s), 1235(s), 1205(s), cm$^{-1}$; $^1$H-NMR (CDCl$_3$)δ(ppm) 1.40(s, 18H), 5.10(m, 2H), 5.60(s, 1H), 6.25(t, 1H), 7.70(s, 2H); $^{13}$C-NMR (CDCl$_3$)δ30.12, 34.36, 78.41, 93.21, 126.64, 129.00, 135.60, 158.34, 190.05, 216.16 ppm.

EXAMPLE 20

Synthesis of 4-(1'-methylidene-5'-hexynyl)-2,6-di-tert-butylphenol

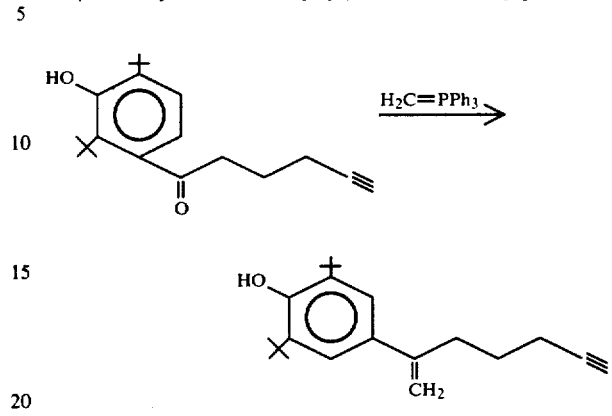

A mixture of 8.19 g (23.0 mmol) of (mthyl)-triphenyl-phosphonium bromide in 50 mL of benzene is treated at 0° with 6.67 mL (18.5 mmol) of 2.76M n-butyllithium. The reaction mixture is heated for 15 minutes at 80° and then is cooled back to room temperature and to it added 1.38 g (4.6 mmol) of 4-(5'-hexnoyl)-2,6-di-t-butylphenol. After heating the mixture at 80° for two hours, it is cooled to 25° and poured into a mixture of water and pentane. The aqueous portion is extracted with pentane and the combined organic phase is washed with sat. NaCl and then dried (MgSO$_4$). The concentrate is purified by flash chromatography (silica gel, 5% EtOAc/hexane, $R_f$=0.53) to afford 1.02 g (74%) of the title compound: IR (CDCl$_3$) 3640(s), 3310(s), 2960(s), 2110(w), 1620(w), 1435(s), 1245(s), 1155(s), 630(s) cm$^{-1}$; $^1$H-NMR (CDCl$_3$)δ(ppm) 1.35(s, 18H), 1.3–2.6(m, 7H), 4.6–5.0(m, 3H), 7.0(s, 2H); $^{13}$C-NMR (CDCl$_3$)δ(off resonance multiplicity) 18.00(t), 27.24(t), 30.35(q), 34.37 (two carbons, s and t), 68.64(d), 84.29(s), 110.68(t), 122.70(d), 131.89(s), 135.46(s), 147.82(s), 153.41(s) ppm.

EXAMPLE 21

Synthesis of 4-((E)-1',6'-heptadien-3'-one)-2,6-di-t-butylphenol

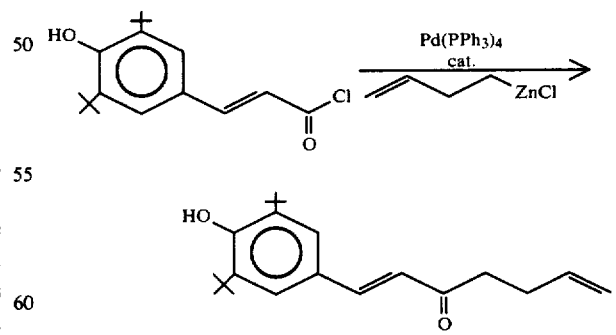

A mixture of 1.63 g (12.0 mmol) of zinc chloride in 15 mL of THF is treated at 0° with 14.3 mL (10.0 mmol) of 0.70M 3-buten-1-ylmagnesium bromide and stirred at room temperature for 30 minutes. The slurry of 3-buten-1-ylzinc chloride thus obtained is then added at 50° to a solution of 1.18 g (4.0 mmol) of (E)-3-(3',5'-di-t-butyl-4'- hydroxyphenyl)propenoyl chloride and 0.23 g (5 mol %) of tetrakis(triphenylphosphine)palladium in 15 mL of THF. After stirring the mixture at 50° for 30 minutes, it is poured into sat. NH$_4$Cl and the layers are separated. The aqueous portion is extracted with pentane and the combined organic phase is washed with sat. NaCl and then dried (MgSO$_4$). The concentrate is purified by flash chromatography (10% EtOAc/hexane, R$_f$=0.35) and recrystallization (heptane) to provide 0.829 g (66%) of the title compound: mp 119°–120°; IR (CCl$_4$) 3640(s), 3080(w), 2965(s), 1655(m), 1595(s), 1425(s), 1155(s) cm$^{-1}$; $^1$H-NMR (CDCl$_3$)δ(ppm) 1.40 (s, 18H), 2.2–2.8 (m, 4H), 4.7–5.0 (m, 2H), 5.45(s, 1H), 5.4–6.0(m, 1H), 6.45(d, J=16 Hz, 1H), 7.25(s, 2H), 7.35(d, J=16 Hz, 1H); $^{13}$C-NMR (CDCl$_3$)δ28.43, 30.15, 34.30, 39.40, 115.09, 123.51, 125.71 (two carbon?), 136.58, 137.42, 144.03, 156.41, 199.57 ppm.

EXAMPLE 22

Synthesis of 4-(2',2'-dimethoxyethyl)-2,6-di-t-butylphenol

In a manner similar to that described hereinbefore in Example 16, 2.96 g (7.91 mmol) of 4-trimethylsilylethynyl-2,6-di-t-butyl-1-trimethylsiloxybenzene (which is prepared from the tetrakis(triphenylphosphine)palladium catalyzed reaction of trimethylsilylethynyl zinc chloride with 2,6-di-t-butyl-4-iodo-1-trimethylsiloxybenzene) is converted into the title compound, which is purified by flash chromatography (silica gel; 5% EtOAc/hexane, R$_f$=0.15): IR (CCl$_4$) 3640(m), 2950(s), 1430(m), 1120(s), 1065(m), 1045(m) cm$^{-1}$; $^1$H-NMR (CDCl$_3$)δ(ppm) 1.40(s, 18H), 2.80(d, J=7 Hz, 2H), 3.20(s, 6H), 4.40(t, J=7 Hz, 1H), 4.95(s, 1H), 6.90(s, 2H); $^{13}$C-NMR (CDCl$_3$)δ30.36, 34.26, 39.38, 52.98, 105.54, 125.92, 127.64, 135.69, 152.35 ppm.

EXAMPLE 23

Synthesis of 4-(5',5'-dimethoxy-3'-pentanone)-2,6di-t-butylphenol

In a procedure similar to that described hereinbefore for Example 16, 1.03 g (2.40 mmol) of 4-(5'-trimethylsilyl-4'-pentyn-3'-one)-2,6-di-t-butyl-1-trimethylsiloxybenzene is converted into 0.195 g (19%) of the title compound, with flash chromatography (10% EtOAc/hexane, R$_f$=0.18) being used as the purification method: IR (CCl$_4$) 3650(m), 2960(s), 1715(m), 1435(s), 1125(s) cm$^{-1}$; $^1$H-NMR (CDCl$_3$)δ(ppm) 1.35 (s, 18H) 2.6(m, 6H), 3.20(s, 6H), 4.65(t, J=7 Hz, 1H), 4.90(s, 1H), 6.85(s, 2H); $^{13}$C-NMR (CDCl$_3$)δ29.50, 30.37, 34.37, 46.11, 46.72, 53.84, 101.73, 124.88, 131.55, 136.01, 152.14, 206.89 ppm.

EXAMPLE 24

Synthesis of 4-(2'-dimethoxymethyl-4'-pentynoyl)-2,6-di-t-butylphenol

In a procedure similar to that described hereinbefore in Example 1, 2.41 g (14.0 mmol) of 2-dimethoxymethyl-4-pentynoic acid (which is prepared from the sequence: esterification of 4-pentynoic acid using methanol, disilylation using excess LDA/chlorotrimethylsilane, titanium tetrachloride promoted reaction with trimethyl orthoformate, and hydrolysis of the ester and silylacetylene moieties with dilute NaOH) is converted into 0.264 g (5%) of the title compound, which is purified by flash chromatography (10% EtOAc/hexane, R$_f$=0.17) and recrystallization (heptane): mp 113°–115°; IR (CDCl$_3$) 3630(s), 3310(m), 2960(s), 1660(s), 1580(m), 1220(s), 1120(s), 1060(s) cm$^{-1}$; $^1$H-NMR (CDCl$_3$)δ(ppm) 1.35 (s, 18H), 1.75(t, J=2 Hz, 1H), 2.45(m, 2H), 3.15(s, 3H), 3.25(s, 3H), 3.75(q, J=7 Hz, 1H), 4.40(d, J=7 Hz, 1H), 5.50(s, 1H), 7.65(s, 2H); $^{13}$C-NMR (CDCl$_3$)δ(off-resonance multiplicity 18.47(t), 30.16(q), 34.41(s), 47.95(d), 53.83(q), 56.13(q), 70.01(d), 81.56(s), 105.85(d), 126.60(d), 129.42(s), 135.59(s), 158.67(s), 198.70(s) ppm.

EXAMPLE 25

Synthesis of 1-(5'-hexynoyl)-3,5-bis(trifluoromethyl)benzene

In a manner similar to that described hereinbefore in Example 8, 4.40 g (15.0 mmol) of 1-bromo-3,5-bis(trifluoromethyl)benzene is converted into 2.40 g (65%) of the title compound, which is purified by flash chromatography (3% EtOAc/hexane, R$_f$=0.24); IR (neat) 3320, 2950(w), 1690(s), 1615(m), 1380(s), 1180(vs), 1140(vs), 910(s), 700(s), 680(s) cm$^{-1}$; $^1$H-NMR (CDCl$_3$)δ(ppm) 1.5–2.2 (m, 5H), 2.90 (t, J=7 Hz, 2H), 7.80(s, 1H), 8.15(s, 2H).

EXAMPLE 26

Synthesis of 4-(6'-heptyn-3'-one)-2,6-di-t-butylphenol and 4-[4'-(2''-propynyl)-6'-heptyn-3'-one]-2,6di-t-butylphenol In a procedure similar to that described hereinbefore in Example 11, 4-(3'-butanone)-2,6-di-t-butylphenol (which is prepared from alkylation of the enolate derived from LDA and acetone with 4-bromomethyl-b 2,6-di-t-butylphenol) is treated with LDA followed by 3-bromo-1-trimethylsilylpropyne (which is prepared from the bromination of 3-hydroxy-1-trimethylsilylpropane with PBr$_3$) to afford a mixture of 4-mono- and 4,4-di-propargylated ketones. The mixture is desilylated using an excess of KF.2H$_2$O in DMF at 60° to 1 h. Flash chromatography then provides the pure isomeric ketones.

4-(6'-heptyn-3'-one)-2,6-di-t-butylphenol: R$_f$ (5% EtOAc/hexane) 0.18; IR (CCl$_4$) 3640(s), 3320(s), 2970(s), 2120(w), 1710(s), 1435(s), 910(s), 635(s) cm$^{-1}$; $^1$H-NMR (CDCl$_3$)δ(ppm) 1.35(s, 18H), 1.75(t, J=2 Hz, 1H), 2.2–2.8(m, 8H), 4.90(s, 1H), 6.80(s, 1H); $^{13}$C-NMR (CDCl$_3$)δ12.92, 29.70, 30.29, 34.27, 41.45, 44.84, 68.74, 83.03, 124.68, 131.34, 135.91, 152.03, 207.71 ppm.

4-[4'-(2''-propynyl)-6'-heptyn-3'-one]-2,6-di-t-butylphenol: mp 71°–72°; R$_f$ (5% EtOAc/hexane) 0.23; IR (CCl$_4$) 3630(s), 3320(s), 2960(s), 2120(w), 1710(s), 1430(s), 635(s) cm$^{-1}$; $^1$H-NMR (CDCl$_3$)δ(ppm) 1.30 (s, 18H), 1.80(t, J=2 Hz, 2H), 2.2–2.8(m, 11H), 4.75(s, 1H), 6.75(s, 2H); $^{13}$C-NMR (CDCl$_3$)δ(off-resonance multiplicity) 19.61(t), 29.43(t), 30.26(q), 34.24(s), 44.72(t), 49.21(d), 70.60(d), 80.74(s), 124.76(d), 131.42(s), 135.91(s), 152.03(s), 209.33(s) ppm.

EXAMPLE 27

Alternative synthesis of
4-(5'-hexynoyl)-2,6-di-tert-butylphenol

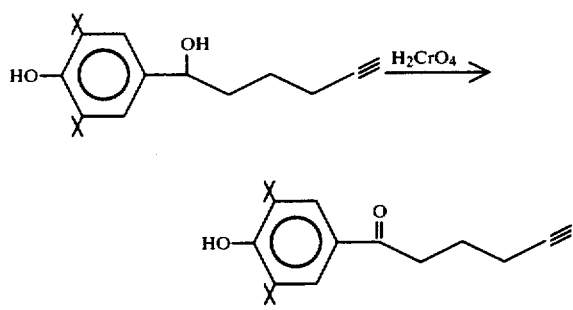

A solution of 4-(1'-hydroxy-5'-hexynyl)-2,6-di-tert-butylphenol (which is prepared as in Example 10 hereinbefore) in THF is treated at 0° with excess Jones reagent and then stirred at room temperaure for eight hours. The reaction mixture is poured into saturated NaCl and the aqueous layer is extracted with pentane. The combined organic phase is washed with sat. NaCl and dried (MgSO$_4$). The concentrate is purified as described hereinbefore in Example 1 to give the title compound.

EXAMPLE 28

Alternative synthesis of
4-(5'-hexynoyl)-2,6-di-tert-butylphenol

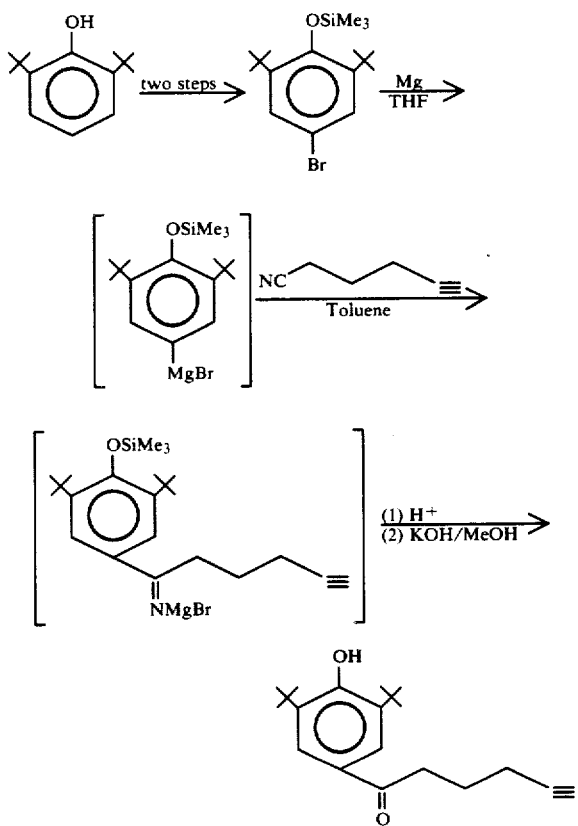

Large scale preparation of this compound may be achieved by utilizing the above-described reaction scheme as described hereinafter.

A flame dried 500 ml reaction flask is charged with 89.3 g (0.25 mol) of 2,6-di-tert-butyl-4-bromo-1-trimethylsiloxybenzene, (which is prepared as described hereinbefore in Example 1), 12.0 g (0.50 mol) of magnesium metal shavings, and 300 ml of dry THF under argon. After adding a few drops of dibromoethane at 60° C. to initiate the Grignard formation, the reaction is stirred for 2 hrs a reflux temperature. A GLC of an aliquot neutralized with NH$_4$Cl solution indicates that no starting bromide remains. The heat is removed from the reaction and the liquid content of the flask is transferred to a flame dried 1 liter single neck round bottom flask by means of argon pressure and a double-tip needle through rubber septa. An additional 150 ml dry THF is used to wash the magnesium turnings and the reaction flask to ensure complete transfer. The solvent is removed on the Rotavapor, first using aspirator vacuum then a vacuum pump for 20–30 minutes. Each time the vacuum is broken by allowing only argon back into the Rotavapor apparatus. The flask is then charged with 500 ml dry Et$_2$O and stirred for 0.5 hr at reflux to dissolve or suspend the Grignard reagent. A solution of 18.6 g (0.20 mol) 5-cyano-1-pentyne (Farchan Laboratories, Gainesville, Fla.) in 30 ml Et$_2$O is then added by means of an additional funnel. The reaction mixture is stirred for 2 hrs at reflux with 150 ml of the Et$_2$O being removed by distillation during the last 0.5 hr. The reaction mixture is cooled in an ice bath and quenched with 50 ml of 15% NH$_4$Cl solution. A 200 ml portion of 10% HCl is carefully added to the reaction mixture which is then stirred overnight at ambient temperature. The reaction mixture is then poured into a separatory funnel containing 500 ml 10% NaCl. The layers are separated and the aqueous phase is extracted a second time with 300 ml Et$_2$O. The combined Et$_2$O solutions are dried over MgSO$_4$, filtered and evaporated. The residue is dissolved in 500 ml MeOH/250 ml THF. A 50 ml portion of 1N KOH is added to the flask and the mixture is stirred for 2 hrs at ambient temperature. The reaction mixture is then poured into a 2 liter separatory funnel containing 700 ml 10% NH$_4$Cl and 75 ml of 1N HCl and extracted twice with Et$_2$O. The Et$_2$O extracts are washed once with 10% NaCl solution, dried over MgSO$_4$, filtered and evaporated to give a residue of 73 g of crude product.

In order to determine the purified yield on this pilot run, a 10 g portion of the crude product is flash chromatographed on a 40 mm × 300 mm column of silica gel 60 using 95 hexane:5 EtOAc taking 50 ml cuts. A total of 6.1 g of 99+% pure title compound is collected (73% yield). The remainder of the crude product (63 g) is dissolved in 240 ml of iso-octane and seeded with a few crystals of pure title compound. The product is then allowed to crystallize at 0° C. to give a yield of 23 g. The mother liquor is evaporated and the residue is flash chromatographed in two 20 g batches on a 50 mm × 400 mm column of silica gel 60 (230–400 mesh) using 95 hexane:5 EtOAc and taking 175 ml cuts. The product from this chromatography is combined with the material obtained by crystallization (35 g total) and given a final recrystallization from 500 ml of EtOH/H$_2$O (70:30 v/v). The recrystallization solution is seeded at 25° C., cooled to 0° C. overnight in the refrigerator, and filtered to give 28.8 g of title compound.

EXAMPLE 29

Carrageenan Rat Paw Edema Test

Male Sprague-Dawley rats (Charles River Laboratories) are weighed and food fasted overnight. The animals are then divided into four to six groups of six animals each according to body weights (average about 145 g) so that each group has about the same average body weight (within 10 g).

The following morning animals are dosed with the test compound and then placed in individual cages. For oral dosing, the drug is suspended in 0.5% methyl cellulose with 2% Tween 80, and delivered via stomach tube in a 5 ml volume.

Paw volumes (0 time) are determined on both hind paws with a mercury displacement device equipped with a transducer and digitizer. One hour after dosing the test compound, the animals are placed in a plastic restrainer and 50 ul of a 1% (w/w) carrageenan solution in 0.9% saline is injected into the ventral surface of the left rear paw. Four hours after the carrageenan injection, the paw volumes are again determined.

The results are expressed as percent inhibition of the mean paw volume of the test group relative to the control group. Statistical differences are determined by one way analysis of variance. $ID_{35}$ values are determined by regression analysis.

TABLE 1

Carrageenan Rat Paw Edema Test Results

| Compound No. | Percent Inhibiton at 100 mg/kg dose P.O* | ID35 (mg/kg) |
|---|---|---|
| 1 | 65.0 | 40.0 |
| 2 | 75.6 | 46.8 |
| 3 | 66.9 | 9.9 |
| 4 | 64.9 | — |
| 5 | 61.3 | 8.1 |
| 6 | 71.2 | 3.3 |
| 7 | 53.6 | — |
| 8 | 50.4 | — |
| 9 | 41.7 | — |
| 10 | 92.2 | 24.5 |
| 11 | 67.6 | 4.8 |
| 12 | 59.9 | 11.4 |
| 13 | 69.8 | 17.9 |
| 14 | 54.4 | 30.0 |
| 15 | 75.7 | 55.2 |
| 16 | 25.7 | — |
| 17 | 75.5 | 4.4 |
| 18 | 72.0 | 2.5 |
| 19 | 71.7 | 45.3 |
| 20 | 73.1 | 34.2 |
| 21 | 41.7 | ~90.0 |
| 22 | 47.0 | — |
| 23 | 67.9 | 17.4 |
| 26 | 43.3 | 110.0 |
| 27 | 62.8 | 28.3 |
| 29 | 70.7 | 28.2 |
| 30 | 72.8 | 35.2 |
| 32 | 50.8 | — |
| 34 | 66.1 | — |
| 35 | 61.1 | — |

*All values are statistically significantly different from control group at P ≦0.05.

EXAMPLE 30

Oxazolone-Induced Inflamed Mouse Ear Test ("Ox-IMET")

Adult male Cox ICR mice, 25–35 g, are sensitized by applying 3% oxazolone in olive oil to the clipped abdomen of each animal using a cotton swab. One week later, the mice are challenged on the inner surface of the left ear with 3% oxazolone in acetone. At the same time 25 ul of the test compound (10% in ethanol) is applied to the outer surface of the same ear. Twenty four hours after the challenge, the animals are sacrificed by cervical dislocation and both ears are removed. A 5 mm punch biopsy is removed from both ears and is weighed to the nearest 0.1 mg on a Cahn electrobalance. Ten animals are used per group. The study usually consists of 4 to 6 groups, of which one is a control group which is challenged on the left ear, but is not treated with a test compound. The results are expressed as percent inhibition of the swelling response compared to the control group. Statistical tests for significance between groups are made using a one way analysis of variance of the ear weight differences.

TABLE 2

Ox-IMET Test Results

| Compound No. | Percent Inhibition* |
|---|---|
| 2 | 27.3 |
| 5 | 25.3 |
| 6 | 46.0 |
| 7 | 40.9 |
| 8 | 38.3 |
| 9 | 23.2 |
| 11 | 34.1 |
| 12 | 29.7 |
| 15 | 39.6 |
| 16 | 30.3 |
| 17 | 59.5 |
| 18 | 54.5 |
| 24 | 38.2 |
| 25 | 40.4 |
| 28 | 37.4 |
| 30 | 33.4 |
| 32 | 44.5 |
| 33 | 54.1 |

*All values are statistically significantly different from control group at P≦0.05.

EXAMPLE 31

Arachidonic Acid-Induced Inflamed Mouse Ear Test

Adult male Cox ICR mice, 25–35 g, are treated on the inside of the left ear with 25 ul of a 2.5% solution of arachidonic acid (with and without drugs) in a vehicle consisting of acetone:pyridine:water (97:2:1, w/w/w). All drugs are dissolved with arachidonic acid in the vehicle. At the end of 3 hours, animals are sacrificed by cervical dislocation and both ears are removed. A 5 mm punch biopsy is removed from both ears and is weighed to the nearest 0.1 mg on a Cahn electrobalance. Ten animals are used per group. The study usually consists of 4 to 6 groups, of which one is a control group which is treated on the left ear with only arachidonic acid in the vehicle. The results are expressed as percent inhibition of the swelling response compared to the control group. Statistical tests for significance between groups are made using a one way analysis of variance of the ear weight differences. $ID_{50}$ values are determined by regression analysis.

TABLE 3

Arachidonic Acid-Induced Inflamed Mouse Ear Test Results

| Compound No. | Percent Inhibition at 50 ug/ear topical dose* | ID50 (ug/ear) |
|---|---|---|
| 3 | 61.6 | 22.7 |
| 4 | 79.6 | 6.6 |
| 10 | 64.9 | — |
| 11 | 43.9 | 20.7 |
| 13 | 74.4 | 17.5 |
| 27 | 34.8 | 52.4 |
| 30 | 69.1 | 29.5 |

TABLE 3-continued

| Arachidonic Acid-Induced Inflamed Mouse Ear Test Results | | |
|---|---|---|
| | Percent Inhibition at | |
| Compound No. | 50 ug/ear topical dose* | ID50 (ug/ear) |
| 31 | 82.8 | 15.3 |

*All values are statistically significantly different from control group at $P \leq 0.05$.

EXAMPLE 32

Adjuvant Arthritis Methodology (a) Therapeutic

Male Sprague-Dawley rats weighing 167-170 gm are allowed to acclimate to the laboratory for at least 3 days. Ten rats are then assigned to the healthy control group and the remaining rats are assigned to the arthritic group. On day 0, the rats in the arthritic group are injected subcutaneously in the middle of their tail with a modified Freund's adjuvant (MFA) at a dosage of 0.05 ml/100 gm body weight. The MFA is made by grinding *Mycobacterium butyricum* (Mb) and then mixing with mineral oil at a concentration of 10 mg Mb/ml of mineral oil. This is mixed in an Omni mixer for 45 minutes.

Paw volumes and body weights are determined on days −1, 6, 13, 19, 26, and 29. On day 19, paw volume changes from day −1 are determined for the arthritic group. The rats with paw volume changes $\geq 0.50$ ml but $\leq 2.50$ ml are randomized by paw volume changes into the treatment groups on day 20. On days 20 through 28, the rats are orally dosed twice a day (once a day on weekends). On day 29, two representative rats from each treatment group are photographed, paw volumes and body weights are determined, and then the rats are sacrificed with $CO_2$ and x-rays are taken.

The radiographs are used to grade bone resorption. Bone resorption is graded in 20 areas of the fore and hind paws. The areas for grading on the hind paw are: distal femur end, proximal tibia and tibula, distal end of the tibia and the small bone under the tibia, calcaneous, tarsus, and metatarsus. The areas on the fore paws are: radius, ulna, carpus, and metacarpus. Each area is given a grade of 0 (no resorption) or 1 (resorption) for possible grade of 20 of each animal.

| Adjuvant Arthritis Data - Therapeutic | | | | | |
|---|---|---|---|---|---|
| Com-pound | Treatment | | Paw Volume % Decrease | Body Weights % Increase | Bone Resorption % Inhibition |
| | (mg/kg) | (x/day) | | | |
| 11 | 5 | 2 | 75 | 36 | 37 |
| 11 | 15 | 2 | 83 | 34 | 50 |
| Indo-meth-acin | 0.5 | 1 | 43 | 7 | 15 |

(b) Immunomodulatory

The same procedures as for the therapeutic, except the rats are randomly assigned to the treatment groups including the healthy control group by body weights on day −2. Paw volumes and body weights are determined on days −1, 6, 13, 20, and 27. The rats are treated from day −1 through day 7. The rats are sacrificed on day 28 and x-rayed. The radiographs are graded as above using a severity scale from 0 (no resorption) to 3 (severe resorption).

| Adjuvant Arthritis Data - Immunomodulatory | | | | | |
|---|---|---|---|---|---|
| Com-pound | Treatment | | Paw Volume % Decrease | Body Weights % Increase | Bone Resorption % Inhibition |
| | (mg/kg) | (x/day) | | | |
| 11 | 15 | 2 | 48 | 30 | 57 |

EXAMPLE 33

Pharmaceutical Compositions in Tablet Form

Tablets are prepared by conventional methods, such as mixing and direct compaction, formulated as follows:

| Ingredient | mg per tablet |
|---|---|
| Compound 11 | 200 |
| Microcrystalline cellulose | 100 |
| Sodium starch glycolate | 30 |
| Magnesium stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

Similar results are achieved with tablets formulated as above but replacing the 200 mg of Compound 11 with: 300 mg of Compound 10; 400 mg of Compound 17; 350 mg of Compound 18; or 100 mg of Compound 29.

EXAMPLE 34

Pharmaceutical Compositions in Capsule Form

Capsules are prepared by conventional methods, comprised as follows:

| Ingredient | mg per capsule |
|---|---|
| Compound 11 | 200 |
| Lactose | To fill to volume of capsule |

The above capsule administered orally once a day substantially reduces the symptomology in a patient afflicted with rheumatoid arthritis or osteoarthritis. Similar results are achieved with capsules formulated as above but replacing Compound 11 with Compounds 10, 17, 18, or 29.

What is claimed is:

1. An anti-inflammatory compound having the structure:

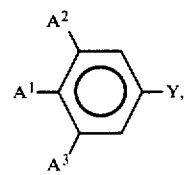

wherein:

(a) $A^1$ is selected from the group consisting of —OH, —H, and —$O_2CR$; wherein R is a straight or branched chain alkyl group having from 1 to about 10 carbon atoms;

(b) $A^2$ and $A^3$ are independently selected from the group consisting of —C(CH$_3$)$_3$, —Si(CH$_3$)$_3$, and —CF$_3$; and (c) Y is selected from the group consisting of:

(1) —(CR$^1$$_2$)$_n$—C≡C—H, wherein n is an integer from 1 to about 6;

(2)

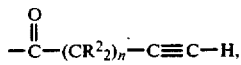

wherein n is an integer from 0 to about 5;

(3)

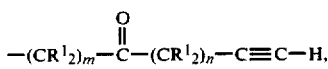

wherein m is an integer from 1 to about 5, and m+n is an integer from 1 to about 5;

(4)

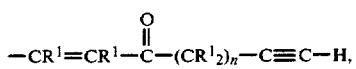

wherein n is 0 or 1;

(5) —(CR$^1$$_2$)$_n$—CR$^3$=CH$_2$, wherein n is an integer from about 2 to about 6;

(6)

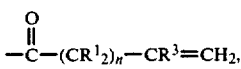

wherein n is an integer from 0 to about 5;

(7)

wherein m is an integer from 1 to about 3, and m+n is an integer from 1 to about 3;

(8)

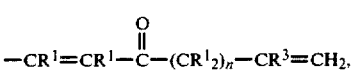

wherein n is an integer from 0 to about 3;

(9) —(CR$^1$$_2$)$_n$—CR$^3$=C=CH$_2$, wherein n is an integer from 0 to about 6;

(10)

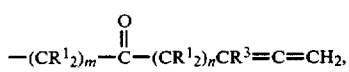

wherein m+n is an integer from 0 to about 5;

(11)

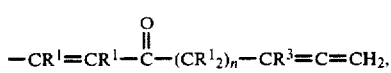

wherein n is an integer from 0 to about 3;

(12) —(CR$^1$$_2$)$_n$—CH(ZR$^4$)$_2$, wherein n is an integer from 1 to about 6; and (13)

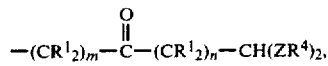

wherein n is an integer from 1 to about 5, m is an integer from 0 to about 4, and m+n is an integer from about 1 to about 5;

and wherein each $R^1$ is independently selected from the group consisting of —H, —OR$^3$, —NR$^3$$_2$, —NR$^3$$_3$$^+$, —N(R$^3$)C(O)R$^3$, —O$_2$CR$^3$, —CO$_2$R$^3$, C(O)NR$^3$$_2$, straight or branched chain saturated alkyl group having from 1 to about 3 carbon atoms, and straight or branched chain unsaturated alkyl group having from 1 to about 3 carbon atoms; each $R^2$ is independently selected from the group consisting of —H, —OR$^3$, —NR$^3$$_2$, —NR$^3$$_3$$^+$, —N(R$^3$)C(O)R$^3$, —O$_2$CR$^3$, —CO$_2$R$^3$, C(O)NR$^3$$_2$, straight or branched chain saturated alkyl group having from 1 to about 3 carbon atoms, and straight or branched chain unsaturated alkyl group having from 1 to about 2 carbon atoms; each $R^3$ is independently selected from the group consisting of —H, methyl and ethyl; each $R^4$ is independently selected from the group consisting of —CH$_3$ and —CH$_2$CH$_3$, or the $R^4$'s may be joined to form a cyclic acetal such that both $R^4$'s together are one group selected from —(CH$_2$)$_2$— and —(CH$_2$)$_3$—; and each Z is independently selected from the group consisting of O, S, NH, and NR$^4$; or the pharmaceutically-acceptable salt thereof.

2. An anti-inflammatory compound according to claim 1 wherein $A^1$ is OH or H; and both $A^2$ and $A^3$ are the same group selected from the group consisting of —C(CH$_3$)$_3$, —Si(CH$_3$)$_3$ and —CF$_3$.

3. An anti-inflammatory compound according to claim 2 having the structure:

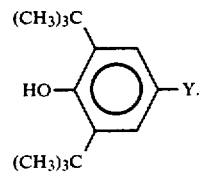

4. An anti-inflammatory compound according to claim 3 wherein:

(a) each $R^1$ and $R^2$ is independently selected from the group consisting of —H, —OH, =CH$_2$, methyl, or ethyl; and wherein further no more than about two $R^1$ or $R^2$ groups are a group other than —H;

(b) each $R^3$ is —H;

(c) each $R^4$ is methyl, or both $R^4$ groups together are the group —(CH$_2$)$_2$— which forms a cyclic acetal; and (d) each Z is independently selected from the group consisting of O or S.

5. An anti-inflammatory compound according to claim 4 wherein the Y group is selected from the group consisting of:

(1) —(CR$^1$$_2$)$_n$—C≡CH, wherein n is an integer from 1 to about 6;

(2)

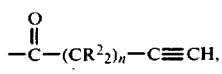

wherein n is an integer from 0 to about 5;

(3)

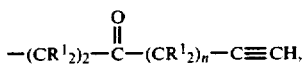

wherein n is an integer from 0 to about 3;

(4)

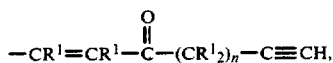

wherein n is 0 or 1;

(5) $-(CR^1{}_2)_n-CH(ZR^4)_2$, wherein n is an integer from 1 to about 6;

(6)

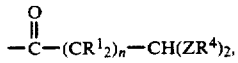

wherein n is an integer from 1 to about 5; and (7)

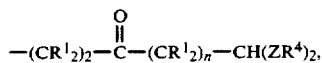

wherein n is an integer from 1 to about 3.

6. An anti-inflammatory compound according to claim 5 wherein the Y group is selected from the group consisting of (1)

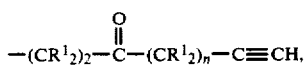

wherein n is an integer from 0 to about 3;

(2)

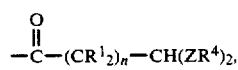

wherein n is an integer from 1 to about 5; and, (3)

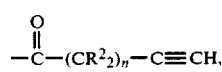

wherein n is an integer from 0 to about 5.

7. An anti-inflammatory compound according to claim 3 having the general formula:

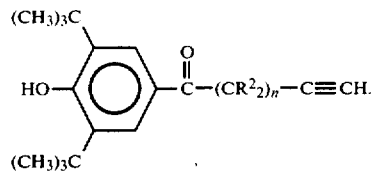

wherein n is an integer from 0 to about 5.

8. An anti-inflammatory compound according to claim 7 wherein each $R^2$ is independently selected from the group consisting of —H, —OH, =$CH_2$, methyl, or ethyl; and wherein further no more than about two $R^2$ groups are a group other than —H.

9. An anti-inflammatory compound according to claim 7 wherein $R^2$ is hydrogen.

10. An anti-inflammatory compound selected from the group of compounds consisting of:
4-propynoyl-2,6-di-t-butylphenol;
4-(1'-hydroxy-2'-propynyl)-2,6-di-t-butylphenol;
4-(3'-butynoyl)-2,6-di-t-butylphenol;
4-butadienoyl-2,6-di-t-butylphenol;
4-(4'-pentynoyl)-2,6-di-t-butylphenol;
4-(4'-pentenoyl)-2,6-di-t-butylphenol;
4-(2'-dimethoxymethyl-4'-pentynoyl)-2,6-di-t-butylphenol;
4-(2',2'-dimethyl-4'-pentynoyl)-2,6-di-t-butylphenol;
4-(3',3'-dimethyl-4'-pentynoyl)-2,6-di-t-butylphenol;
4-(4'-pentyn-3'-one)-2,6-di-t-butylphenol;
4-(5'-hexynoyl)-2,6-di-t-butylphenol;
4-(5'-hexenoyl)-2,6-di-t-butylphenol;
4-(2'-methyl-5'-hexynoyl)-2,6-di-t-butylphenol;
4-(1'-hydroxy-5'-hexynyl)-2,6-di-t-butylphenol;
4-(5'-hexynyl)-2,6-di-t-butylphenol;
4-(1'-methylidene-5'-hexynyl)-2,6-di-t-butylphenol;
4-((S)-(−)-3'-methyl-5'-hexynoyl)-2,6-di-t-butylphenol;
4-((R)-(+)-3'-methyl-5'-hexynoyl)-2,6-di-t-butylphenol;
1-(5'-hexynoyl)-3,5-di-t-butylbenzene;
4-(5'-hexynoyl)-2,6-bis-trimethylsilylphenol;
1-(5'-hexynoyl)-3,5-bis-trimethylsilylbenzene;
1-(5'-hexynoyl)-3,5-bis(trifluoromethyl)benzene;
4-(6'-heptynoyl)-2,6-di-t-butylphenol;
4-(6'-heptyn-3-40 -one)-2,6-di-t-butylphenol;
4-(4'-(2''-propynyl)-6'-heptyn-3'-one)-2,6-di-t-butylphenol;
4-(7'-octynoyl)-2,6-di-t-butylphenol;
4-((E)-1'-penten-4'-yn-3'-one)-2,6-di-t-butylphenol;
4-((E)-1',6'-heptadiene-3'-one)-2,6-di-t-butylphenol;
4-(3',3'-dimethoxypropionyl)-2,6-di-t-butylphenol;
4-(2'-(1'',3''-dioxolane)acetyl)-2,6-di-t-butylphenol;
4-(3',3'-diethoxypropionyl)-2,6-di-t-butylphenol;
4-(2'-(1'',3''-oxathiolane)acetyl)-2,6-di-t-butylphenol;
4-(2',2'-dimethoxyethyl)-2,6-di-t-butylphenol;
4-(5',5'-dimethoxy-3'-pentanone)-2,6-di-t-butylphenol; and
4-(3',3'-dimethyl-5'-hexynoyl)-2,6-di-t-butylphenol,
or the pharmaceutically-acceptable salt thereof.

11. An anti-inflammatory compound according to claim 10 selected from the group of compounds consisting of:
4-(4'-pentyn-3'-one)-2,6-di-t-butylphenol;
4-(5'-hexynoyl)-2,6-di-t-butylphenol;
4-((S)-(−)-3'-methyl-5'-hexynoyl)-2,6-di-t-butylphenol;

4-((R)-(+)-3'-methyl-5'-hexynoyl)-2,6-di-t-butylphenol; and 4-(3',3'-dimethoxypropionyl)-2,6-di-t-butylphenol.

12. The anti-inflammatory compound 4-(5'-hexynoyl)-2,6-di-t-butylphenol, or the pharmaceutically-acceptable salt thereof.

13. A pharmaceutical composition comprising:
(a) a safe and effective amount of an anti-inflammatory compound according to claim 1; and
(b) a pharmaceutically-acceptable carrier.

14. A pharmaceutical composition comprising:
(a) a safe and effective amount of an anti-inflammatory compound according to claim 3; and
(b) a pharmaceutically-acceptable carrier.

15. A pharmaceutical composition comprising:
(a) a safe and effective amount of an anti-inflammatory compound according to claim 6; and
(b) a pharmaceutically-acceptable carrier.

16. A pharmaceutical composition comprising:
(a) a safe and effective amount of an anti-inflammatory compound according to claim 7; and
(b) a pharmaceutically-acceptable carrier.

17. A pharmaceutical composition comprising:
(a) a safe and effective amount of an anti-inflammatory compound according to claim 9; and
(b) a pharmaceutically-acceptable carrier.

18. A pharmaceutical composition comprising:
(a) a safe and effective amount of an anti-inflammatory compound according to claim 11; and
(b) a pharmaceutically-acceptable carrier.

19. A pharmaceutical composition comprising:
(a) a safe and effective amount of an anti-inflammatory compound according to claim 12; and
(b) a pharmaceutically-acceptable carrier.

20. A method for treating diseases characterized by inflammation, said method comprising administering to a human or lower animal in need of such treatment a safe and effective amount of an anti-inflammatory compound of claim 1.

21. A method for treating diseases characterized by inflammation, said method comprising administering to a human or lower animal in need of such treatment a safe and effective amount of an anti-inflammatory compound of claim 7.

22. A method for treating diseases characterized by inflammation, said method comprising administering to a human or lower animal in need of such treatment a safe and effective amount of an anti-inflammatory compound of claim 9.

23. A method for treating diseases characterized by inflammation, said method comprising administering to a human or lower animal in need of such treatment a safe and effective amount of an anti-inflammatory compound of claim 11.

24. A method for treating diseases characterized by inflammation, said method comprising administering to a human or lower animal in need of such treatment a safe and effective amount of an anti-inflammatory compound of claim 12.

* * * * *

UNITED STATES PATENT AND TRADEMARK OFFICE
CERTIFICATE OF CORRECTION

PATENT NO. : 4,708,966
DATED : November 24, 1987
INVENTOR(S) : M. E. Loomans, R. S. Matthews and J. A. Miller It is certified that error appears in the above-identified patent and that said Letters Patent are hereby corrected as shown below:

In the Abstract, line 8, " C=CH$_2$" should be -- $>$C=CH$_2$ --.

In the Abstract, line 9, " C=C=CH$_2$" should be -- $>$C=C=CH$_2$ --.

Column 1, line 34, "osteorthritis" should be --osteoarthritis--.

Column 2, line 24, " C=CH$_2$" should be -- $>$C=CH$_2$ --.

Column 2, line 25, " C=C=CH$_2$" should be -- $>$C=C=CH$_2$ --.

Column 13, line 20, "15901425(s)," should be -- 1590(s), 1425(s), --.

Column 15, lines 30-35, " 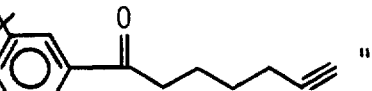 "

should read -- 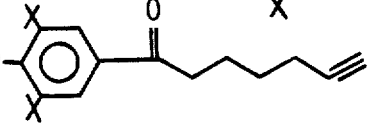 --.

Column 16, line 21, "bis(trimethylsilyl-" should be --bis(trimethylsilyl)- --.

Column 16, line 22, ")acetylene" should be --acetylene--.

Column 16, line 57, "bis(trimethylsilyl-" should be --bis(trimethylsilyl)- --.

Column 16, line 58, ")acetylene" should be --acetylene--.

Column 18, line 55, "ropynoyl-2,6-di-t-butylphenol" should be --propynoyl-2,6-di-t-butylphenol--.

UNITED STATES PATENT AND TRADEMARK OFFICE
CERTIFICATE OF CORRECTION

PATENT NO. : 4,708,966
DATED : November 24, 1987
INVENTOR(S) : M. E. Loomans, R. S. Matthews and J. A. Miller It is certified that error appears in the above-identified patent and that said Letters Patent are hereby corrected as shown below:

Column 19, line 53, "2,6di-t-butylphenol" should be --2,6-di-t-butylphenol--.

Column 21, line 15, "13C-NMR(CDCl$_3$)" should be --$^{13}$C-NMR(CDCl$_3$)--.

Column 21, line 39, "4-(5',5'-dimethoxy-3'-pentanone)-2,6di-t-butylphenol" should be --4-(5',5'-dimethoxy-3'pentanone)-2,6-di-t-butylphenol--.

Column 22, line 32, "4-[4'-(2-propynyl)-6'-heptyn-3'-one]-2,6di-t-butylphenol" should be -- 4-[4'-(2-propynyl)-6'-heptyn-3'-one]2,6-di-t-butylphenol--.

Column 22, line 39, "4-bromoethyl-b" should be -- 4-bromo-ethyl- --.

Column 22, line 46, "to" should be --for--.

Column 32, line 46, "4-(6'heptyn-340-one)-2,6-di-t-butylphenol;"

UNITED STATES PATENT AND TRADEMARK OFFICE
CERTIFICATE OF CORRECTION

PATENT NO. : 4,708,966

DATED : November 24, 1987

INVENTOR(S) : M. E. Loomans, R. S. Matthews and J. A. Miller

It is certified that error appears in the above-identified patent and that said Letters Patent is hereby corrected as shown below:

should be -- 4-(6'heptyn-3-one)-2,6-di-t-butylphenol;  --.

Signed and Sealed this

Fifth Day of July, 1988

Attest:

DONALD J. QUIGG

Attesting Officer

Commissioner of Patents and Trademarks